United States Patent [19]

Uekita et al.

[11] Patent Number: 5,072,262
[45] Date of Patent: Dec. 10, 1991

[54] ELECTRIC-ELECTRONIC DEVICE INCLUDING POLYIMIDE THIN FILM

[75] Inventors: Masakazu Uekita; Hiroshi Awaji, both of Hyogo, Japan

[73] Assignee: Kanegafuchi Kagaku Kogyo Kabushiki Kaisha, Osaka, Japan

[21] Appl. No.: 418,618

[22] Filed: Oct. 10, 1989

Related U.S. Application Data

[63] Continuation of Ser. No. 24,421, Mar. 10, 1987, abandoned.

[30] Foreign Application Priority Data

Mar. 11, 1986 [JP] Japan .................................. 61-54080

[51] Int. Cl.$^5$ ............................................ H01L 49/02
[52] U.S. Cl. ...................................... 357/6; 357/23.15
[58] Field of Search ..................... 357/6, 8, 23.1, 23.15

[56] References Cited

U.S. PATENT DOCUMENTS 4,642,665  2/1987  Lade et al. .............................. 357/6
4,719,281  1/1988  Choe .................................. 307/425

FOREIGN PATENT DOCUMENTS 2321769  3/1977  France .
54-145794  11/1979  Japan .
55-30207  8/1980  Japan .

OTHER PUBLICATIONS

"Method for Preparation of Polyimide Monomolecular Film and Built-Up Film" brochure distributed at Fine Chemical Exposition Mar. 11-13, 1986.
"Polyimide Built-Up Film" a preprint for the annual spring meeting of Japan Chemical Society, Apr. 1, 1986.
Chybicki, M. "Light Emission in MIS Structures with Polymer Films" ACTA Physica Polonica, vol. A48 (1975), pp. 575-577.
Mukai et al, "Planar Multilevel Interconnection . . . " IEEE J. of Solid State Circuits Aug. 1978 pp. 462-467.
Saiki et al, "A New Transistor . . . " J. Electrochem. Soc., Oct. 1977, pp. 1619-1622.
Sato et al, "A Novel Planar Multilevel Interconnection . . . " IEEE Trans. on Parts, Hybrids, and Packaging, Sep. 1973, pp. 176-180.
Alan K. Engel, Tomoko Yoden, Kohei Sanui, and Naoya Ogata, J. Am. Chem. Soc., (1985), 107, 8308-8310.
M. Suzuki, M. Kakimoto, T. Konishi, Y. Imai, M. Iwamoto and T. Hino, Chemistry Letters, (1986), 395-398.
Alan K. Engel, Tomoki Yoden, Kohei Sanui and Naoya Ogata, Polymeric Materials Science and Engineering, 54, (1986), 119-123.
P. S. Vincett and G. G. Roberts, Thin Solid Films, 68, (1980), 135-171.
Chemical Abstracts, vol. 100, No. 10, 5th Mar. 1984, p. 10, Abstract No. 68897m, Columbus, Ohio, U.S.; A. I. Volozhin et al.
Chemical Abstracts, vol. 102, No. 26, Jul. 1, 1985, p. 6, Abstract No. 221283w, Columbus, Ohio, U.S.; L. Minnema et al.
Zalar, Abstract No. 204, Extended Abstracts, vol. 82-2, Oct. 1982, p. 327.
Kakimoto et al, ACS Symp. Ser. Conf., vol. 346 (Polym. High Technol.: Electron Photonics), pp. 485-495, 1987.

Primary Examiner—Andrew J. James
Assistant Examiner—Sara W. Crane
Attorney, Agent, or Firm—Armstrong, Nikaido, Marmelstein, Kubocvik & Murray

[57] ABSTRACT

An electric-electronic device including a polyimide thin film is disclosed, said polyimide thin film having a thickness of not more than 100 Å and a dielectric breakdown strength of not less than $1 \times 10^6$ V/cm. The device has excellent performance properties ascribed to high heat resistance, mechanical strength, chemical resistance and insulating properties of the polyimide thin film.

7 Claims, 12 Drawing Sheets

ELECTRIC-ELECTRONIC DEVICE INCLUDING POLYIMIDE THIN FILM

This application is a continuation of application Ser. No. 024,421 filed Mar. 10, 1987, now abandoned.

FIELD OF THE INVENTION

This invention relates to an electricelectronic device including a heat resistant polyimide thin film excellent in electric insulation properties which is utilized in the field of electronics.

BACKGROUND OF THE INVENTION

In the 1930's, it was found by Langmuir and Blodgett that a fatty acid having from about 16 to about 22 carbon atoms forms a monomolecular film on the surface of water and the film can be built up on a substrate. In recent years, studies on technical applications of the built-up films have been taken up.

The previous studies are summarized, e.g., in *Kotai Butsuri (Solid Physics)*, Vol. 17 (12), p.45 (1982), *Thin Solid Films*, Vol. 68, No. 1 (1980), ibid, Vol. 99, Nos. 1, 2 & 3 (1983), G.I. Gains, *Insoluble Monolayers at Liquid-Gas Interfaces*, Interscience Publishers, New York (1966), etc. Most of the reported applications of a Langmuir-Blodgett film (hereinafter referred to as LB film) to electric-electronic devices concern straight-chain saturated fatty acids or fatty acids having a polymerizable group and esters thereof, and interesting results with respect to initial characteristics have been obtained. However, these LB films are insufficient in heat resistance and other properties and have a problem of insufficient reliability for use in practical electric-electronic devices.

SUMMARY OF THE INVENTION

One object of this invention is to provide an electric-electronic device including a polyimide thin film excellent in heat resistance, mechanical strength, chemical resistance, and electric insulation properties.

It has now been found that the above object can be accomplished by an electric-electronic device in which a polyimide thin film having a thickness of not more than 1000 Å and a breakdown strength of not less than $1 \times 10^6$ V/cm is used, said polyimide thin film having been previously proposed by the present inventors as disclosed in Japanese Patent Application No. 168796/86.

BRIEF DESCRIPTION OF THE ACCOMPANYING DRAWINGS

FIGS. 1 to 7 each illustrates a schematic view of a typical device having a metal/insulating film/semiconductor (MIS) structure.

FIGS. 8 to 10 each illustrates a schematic view of a device having a metal/insulating film/metal (MIM) structure.

FIGS. 11 to 13 each illustrates a schematic view of a device having an insulating film/metal (IM) structure.

DETAILED DESCRIPTION OF THE INVENTION

Figure 1:
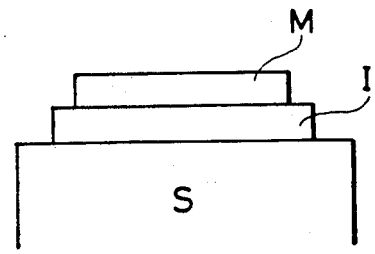

The electric-electronic device according to the present invention can be produced by build-uo of, for example, an amphiphilic polyimide precursor on a substrate, which may, if desired, have been processed beforehand, by the process of Langmuir-Blodgett (hereinafter referred to as LB process) followed by imidation to form a polyimide thin film and, if desired, processing the film afterward.

The amphiphilic polyimide precursor which can be used suitably in the present invention has a repeating unit represented by formula (I) shown below and has a number average molecular weight ranging from 2,000 to 300,000, preferably 10,000 to 150,000.

Formula (I) is represented by

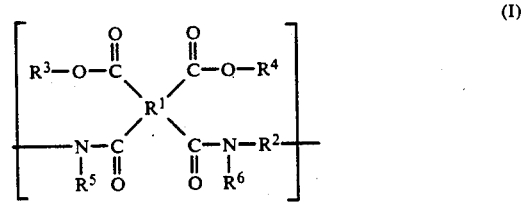

wherein $R^1$ is a tetravalent group having at least 2 carbon atoms, $R^2$ is a bivalent group having at least 2 carbon atoms, and $R^3$, $R^4$, $R^5$ and $R^6$ are hydrogen atom or a monovalent group having 1 to 30 carbon atoms selected from the group consisting of an aliphatic group, an alicyclic group, an aromatic group, a group in which an aliphatic group is combined with an aromatic group or an alicyclic group, and their groups substituted by a halogen atom, nitro group, amino group, cyano group, methoxy group or acetoxyl group, provided that at least one of $R^3$, $R^4$, $R^5$ and $R^6$ is not hydrogen atom and the above-mentioned group which has 1 to 11 carbon atoms.

When the number average molecular weight is outside the above range, the precursor has a tendency that the strength of the film prepared therefrom is too low, or that the viscosity of a solution thereof is too high and accordingly the procedure for forming LB films becomes difficult.

In the formula (I), $R^1$ is a tetravalent group having at least two carbon atoms, preferably 5 to 20 carbon atoms. It may be an aromatic group; an alicyclic group; an aliphatic group; a group wherein an aromatic group and an aliphatic group are combined; a group wherein each of the above-mentioned groups is substituted by a monovalent group having 1 to 30 carbon atoms selected from the group consisting of an aliphatic group, an alicyclic group, an aromatic group, and a group in which an aliphatic group is combined with an alicyclic group or an aromatic group; or a group wherein each of the preceding groups is substituted by a monovalent group such as a halogen atom, nitro group, amino group, cyano group, methoxyl group or acetoxyl group, or by a group in which the above monovalent group bonds to —O—, —COO—, —NHCO—, —CO—, —S—, —CSS—, —NHCS—, —CS—, or the like. Groups characterized by benzenoid unsaturation having at least 6 carbon atoms are preferred as $R^1$ in points of heat resistance, chemical resistance and mechanical properties.

Representative examples of $R^1$ are shown below.

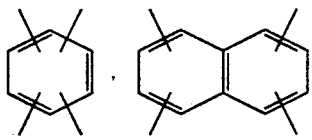

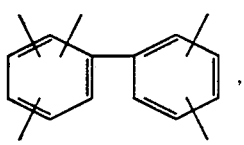

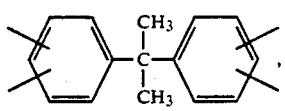

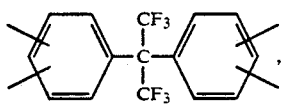

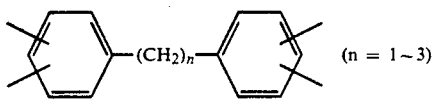 (n = 1~3)

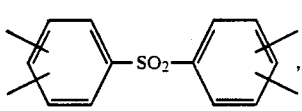

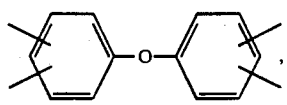

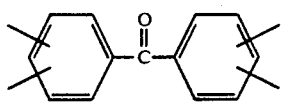

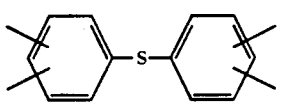

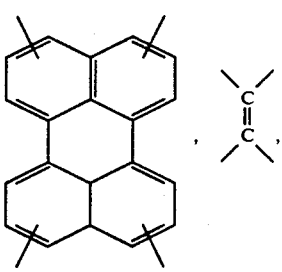

The Terminology "benzoid" as used herein means the same structure as a carbon ring contained in ordinary aromatic compounds, being used in comparison with "quinoid" as illustrated below.

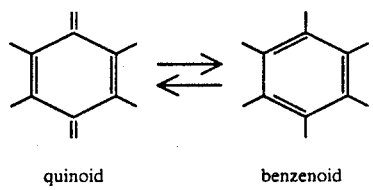

quinoid      benzenoid

In formula (I), the positions in $R^1$ at which the four groups,

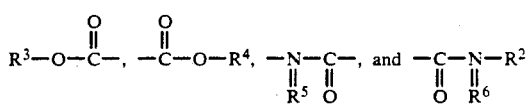

are bonded are not particularly limited, but it is preferable that each pair of these groups are bonded to two adjacent carbon atoms constituting $R^1$ because such a polyimide precursor easily forms a 5-membered ring upon imidation.

Preferable examples of the group $R^1$ as mentioned above are, for instance,

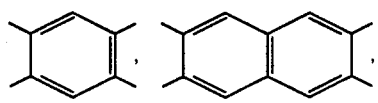

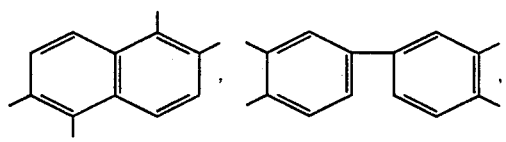

-continued

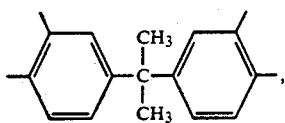

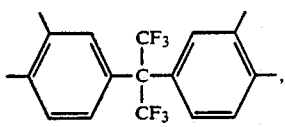

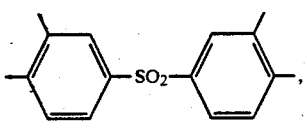

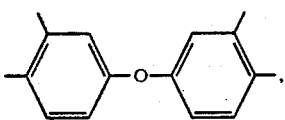

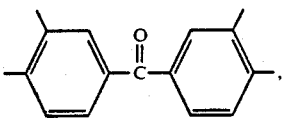

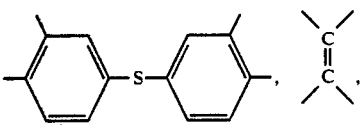

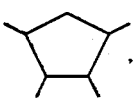

and the like.

In addition, a group of

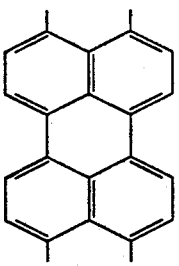

is also preferred as R¹.

The group R² in the formula (I) is a bivalent group having at least 2 carbon atoms. It may be an aromatic group; an aliphatic group; an alicyclic group; a group wherein an aromatic group and an aliphatic group are combined; a group wherein each of the above-mentioned bivalent groups is substituted by a monovalent group having 1 to 30 carbon atoms selected from the group consisting of an aliphatic group, an alicyclic group, an aromatic group and a group in which an aliphatic group is combined with an alicyclic group or an aromatic group; or a group wherein each of the preceding groups is substituted by a monovalent group such as a halogen atom, nitro group, amino group, cyano group, methoxyl group or acetoxyl group, or by a group in which the above monovalent group bonds to —O—, —COO—, —NHCO—, —CO—, —S—, —CSS—, —NHCS—, —CS—, or the like. Groups characterized by benzenoid unsaturation having at least 6 carbon atoms are preferred as the group R² in points of heat resistance, chemical resistance and mechanical properties.

Representative examples of the above-described groups for R² include:

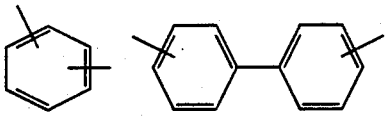

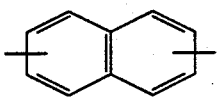

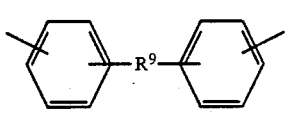

wherein R⁹ represents —(CH₂)$_m$— (m represents an integer of from 1 to 3),

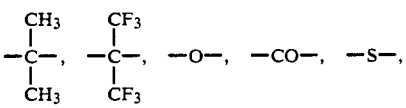

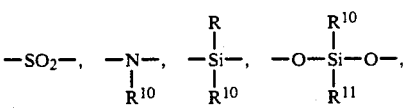

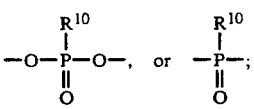

in which R¹⁰ and R¹¹ are an alkyl or aryl group having from 1 to 30 carbon atoms.

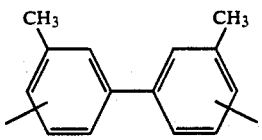

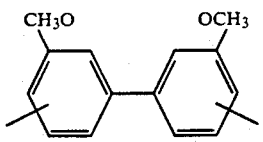

-continued

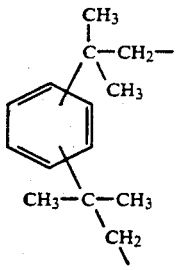

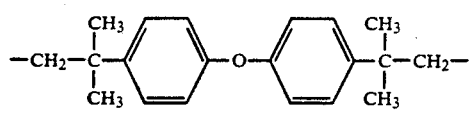

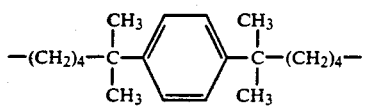

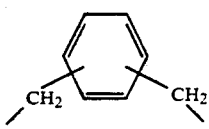

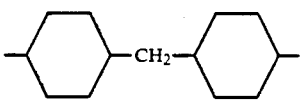

—(CH$_2$)$_P$— (P = 2~10)  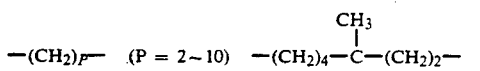

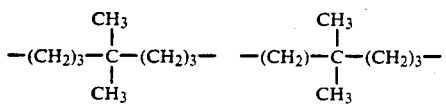

—(CH$_2$)$_{10}$CH—CH$_3$
—(CH$_2$)$_3$—O—(CH$_2$)$_2$O—(CH$_2$)$_3$—

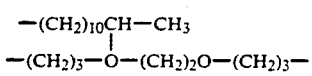  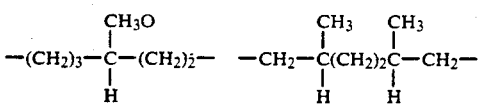

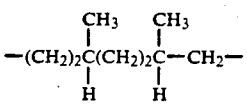

Preferable examples of the above-described preferred groups as R$^2$ include:

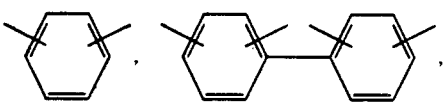

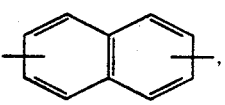

-continued

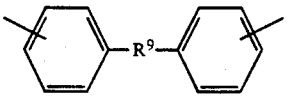

wherein R$^9$ is as defined above.

Each of the groups R$^3$, R$^4$, R$^5$ and R$^6$ in the formula (I) is hydrogen atom or a monovalent group having 1 to 30 carbon atoms, preferably 1 to 22 carbon atoms, such as a monovalent aliphatic group, a monovalent alicyclic group, a monovalent aromatic group, a monovalent group wherein an aliphatic group is combined with an aromatic group or an alicyclic group, or their halogen, nitro, amino, cyano, methoxy or acetoxy substituted groups. R$^3$, R$^4$, R$^5$ and R$^6$ are groups that are introduced to a polyamic acid unit represented by formula (VIII) shown below for the purpose of imparting hydrophobic properties to the polyamic acid unit to thereby obtain a stable condensed film.

Formula (VIII) is represented by

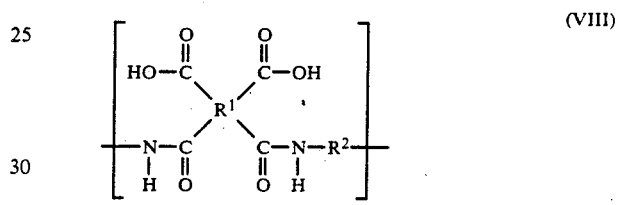

(VIII)

wherein R$^1$ and R$^2$ are as defined above.

It is essential for forming a stable condensed film on water and building up the condensed film on a substrate by the LB process that at least one, and preferably two, of R$^3$, R$^4$, R$^5$, and R$^6$ are the above-defined groups other than a hydrogen atoms and those having from 1 to 11 carbon atoms, and preferably from 1 to 15 carbon atoms.

Representative examples of R$^3$, R$^4$, R$^5$ and R$^6$ other than a hydrogen atom and those having from 1 to 11 carbon atoms are:

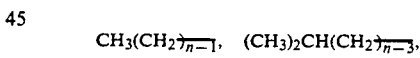

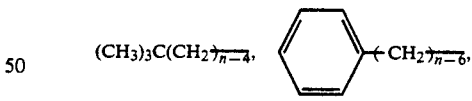

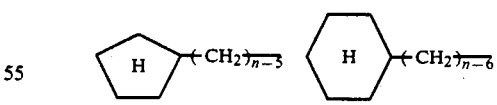

wherein n represents an integer of from 12 to 30, and preferably from 16 to 22.

In view of performance properties achieved and cost incurred, the most preferred among them are straight alkyl groups represented by CH$_3$(CH$_2$)$_{n-1}$, wherein n is as defined above. Although the above-recited substituents for R$^3$, R$^4$, R$^5$, and R$^6$, e.g., a halogen atom, a nitro group, an amino group, a cyano group, a methoxy group, an acetoxy group, etc., are not essential, groups containing a fluorine atom are preferred since presence of a fluorine atom in place of a hydrogen atom brings about a marked improvement on hydrophobic properties.

The amphiphilic polyimide precursor recurring units of formula (I) wherein two of $R^3$, $R^4$, $R^5$, and $R^6$ are hydrogen atoms include those represented by formulas (II) and (III) shown below.

Formula (II) is represented by

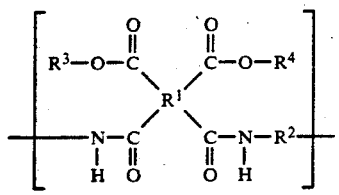

(II)

wherein $R^1$, $R^2$, $R^3$, and $R^4$ are as defined above, with proviso that $R^3$ and $R^4$ do not represent a hydrogen atom or a group having from 1 to 11 carbon atoms.

Formula (III) is represented by

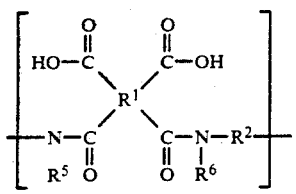

(III)

wherein $R^1$, $R^2$, $R^5$, and $R^6$ are as defined above, with proviso that $R^5$ and $R^6$ do not represent a hydrogen atom or a group having from 1 to 11 carbon atoms.

The amphiphilic polyimide precursor having a recurring unit represented by formula (II) or (III) is preferred in view of ease in preparation and cost.

Representative examples of the amphiphilic polyimide precursor having the recurring unit represented by any of formulas (I), (II), and (III) are:

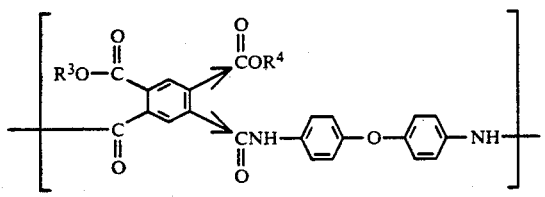

wherein $R^3$ and $R^4$ specifically include $CH_3(CH_2)_{11}$, $CH_3(CH_2)_{13}$, $CH_3(CH_2)_{15}$, $CH_3(CH_2)_{17}$, $CH_3(CH_2)_{19}$, $CH_3(CH_2)_{21}$, $CF_3(CH_2)_{15}$, etc.); and the arrow indicates isomerism (hereinafter the same);

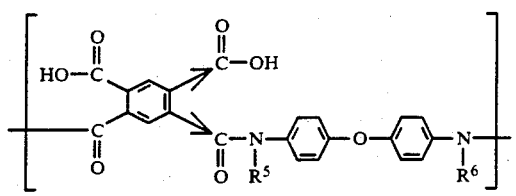

wherein $R^5$ and $R^6$ specifically include $CH_3(CH_2)_{11}$, $CH_3(CH_2)_{13}$, $CH_3(CH_2)_{15}$, $CH_3(CH_2)_{17}$, $CH_3(CH_2)_{19}$, $CH_3(CH_2)_{21}$, $CH_3(CH_2)_{15}$, etc.;

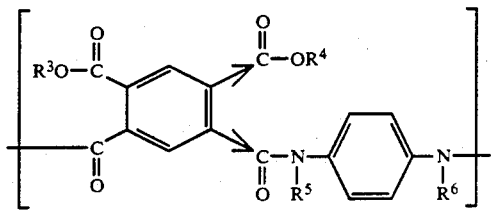

wherein $R_3$ and $R_4$ specifically include $CH_3(CH_2)_{11}$, $CH_3(CH_2)_{13}$, $CH_3(CH_2)_{15}$, $CH_3(CH_2)_{17}$, $CH_3(CH_2)_{19}$, $CH_3(CH_2)_{21}$, $CF_3(CH_2)_{15}$, etc.; and $R^5$ and $R^6$ specifically include $CH_3$, $CH_2(CH_2)_2$, $CH_3(CH_2)_3$, $CH_3(CH_2)_5$, etc.; and

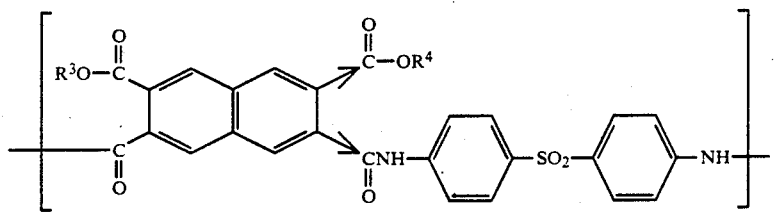

wherein $R_3$ and $R_4$ specifically include $CH_3(CH_2)_{11}$, $CH_3(CH_2)_{13}$, $CH_3(CH_2)_{15}$, $CH_3(CH_2)_{17}$, $CH_3(CH_2)_{19}$, $CH_3(CH_2)_{21}$, $CF_3(CH_2)_{15}$, etc.

In these formulas, the arrow indicating isomerism means that the respective formula includes two isomers. For instance, the formula

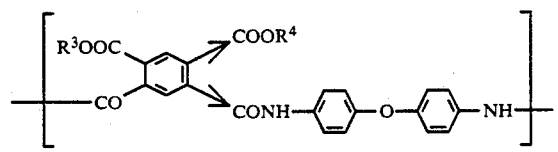

includes isomers (a) and (b) as illustrated below.

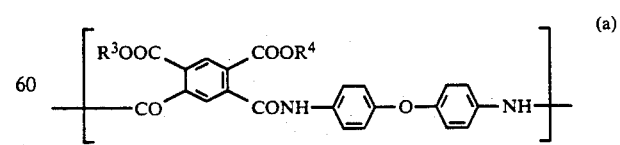

(a)

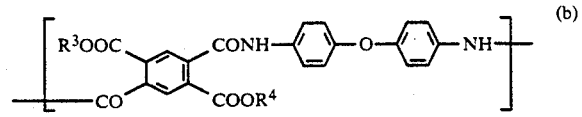

(b)

In the present invention, the respective formula for the amphiphilic polyimide precursor recurring unit may comprise either one of (a) and (b) alone or a combination of (a) and (b).

In general, the amphiphilic polyimide precursors according to the present invention are easily soluble in organic polar solvents, such as N,N-dimethylacetamide, N,N-dimethylformamide, N,N-diethylformamide, hexamethylphosphoramide, and so on; soluble in a mixed solvent of such an organic polar solvent and an ordinary organic solvent, e.g., chloroform; and sparingly soluble or insoluble in ordinary organic solvents, such as benzene, ether, chloroform, acetone, methanol, etc.

The amphiphilic polyimide precursors of the invention show infrared absorptions characteristic of an amido group, a carboxyl group or an ester thereof, and a long-chain alkyl group. They are also characterized by their thermal analysis showing a sudden weight loss starting at about 200° C. and reaching a constant weight at about 400° C. After a constant weight is reached, absorptions characteristic of an amido group, a carboxyl group or an ester thereof, and a long-chain alkyl group disappear and, in turn, an absorption characteristic of an imide ring appears.

While the foregoing description has been directed to the amphiphilic polyimide precursors comprising the repeating unit of formula (I), the object of this invention can be achieved as well by various copolymers as easily anticipated. Examples of these copolymers include those wherein at least one of $R^1$, $R^2$, $R^3$, $R^4$, $R^5$ and $R^6$ comprises at least two different groups selected from the representative examples recited for the respective groups. Examples of such copolymers include those in which two groups are selected for $R^1$ as represented by formula

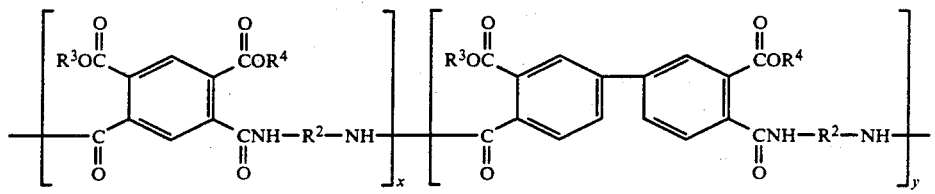

wherein x and y show ratio, $0<x<1$, $0<y<1$, and $x+y=1$ (hereinafter the same); those in which two groups are selected for $R^2$ as represented by formula

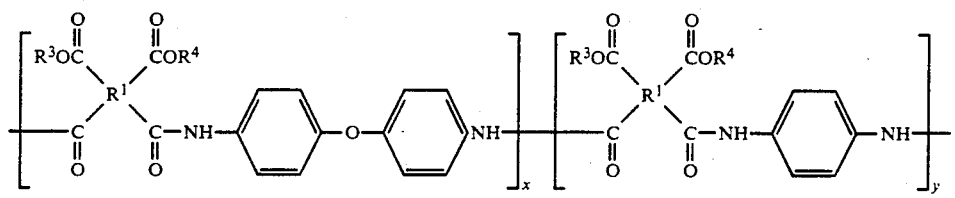

and those in which two or more different groups are selected for any of $R^3$, $R^4$, $R^5$, and $R^6$, e.g., those represented by formula

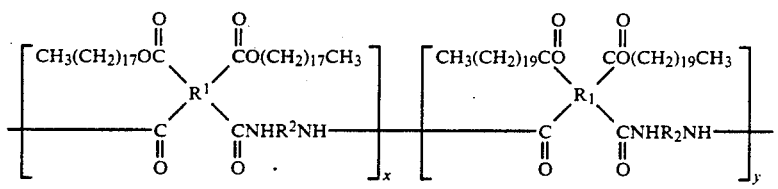

Other examples of the copolymers which can also be used and are more important in the present invention are those in which $R^1$ and/or $R^2$ is/are partly replaced with a group having a different valence. The group to be replaced for a part of $R^1$ is selected from groups containing at least two carbon atoms and having a valence other than 4, e.g., 2 or 3, and preferably 3. In this case, the copolymer is represented by either of the following formulas:

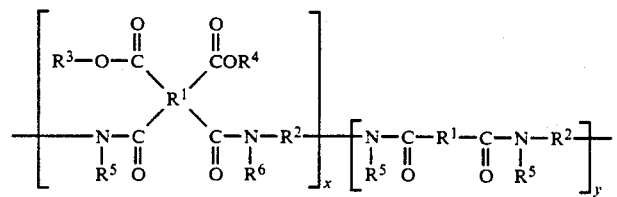

-continued

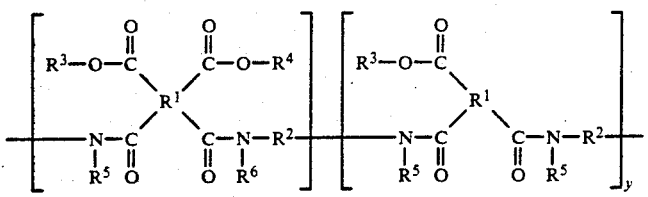

wherein $R^1$, $R^2$ on the left side, $R^3$, $R 4$, $R^5$, and $R^6$ are as defined above; $R^1$ on the right side represents a divalent (upper formula) or trivalent (lower formula) group containing at lest two carbon atoms.

The group to be replaced for a part of $R^2$ is selected from groups containing at least two carbon atoms and having a valence other than 2, and preferably a valence of 3 or 4. In this case, the copolyumer is represented by either of the following formulas:

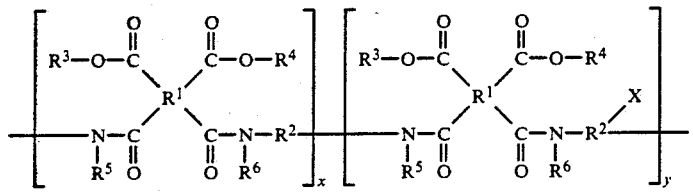

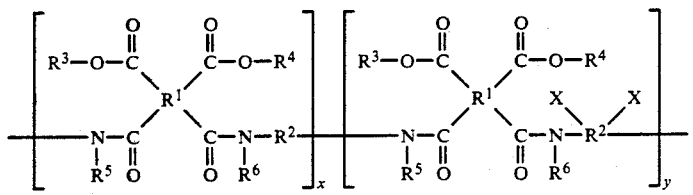

wherein $R^1$, $R^2$ on the left side, $R^3$, $R 4$, $R^5$, and $R^6$ are as defined above; $R^2$ on the right side represents a trivalent (upper formula) or tetravalent (lower formula) group having at least two carbon atoms; and X represents a substituent on $R^2$, and preferably —NHR, —CONHR, etc., wherein R represents an alkyl group or a hydrogen atom.

Modification of the amphiphilic polyimide precursors by the above-mentioned copolymerization is important and preferable for improving build-up characteristics of the polyimide precursors in the LB process as well as physical properties of the polyimide thin film obtained by imidizing the precursor built-up on a substrate.

Representative examples of the group to be replaced for a part of $R^1$ and/or $R^2$ are shown below.

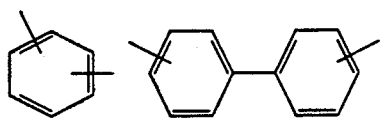

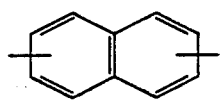

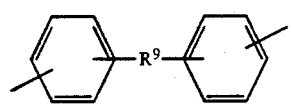

$R^9$ is as defined above,

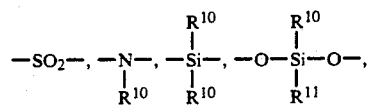

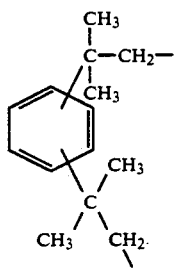

wherein $R^{10}$ and $R^{11}$ each represents an alkyl or aryl group.

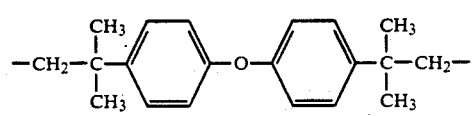

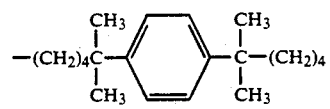

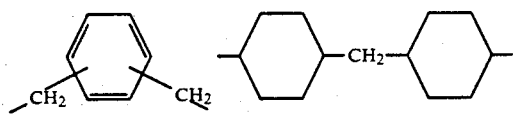
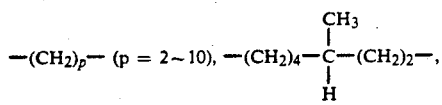
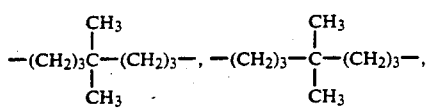
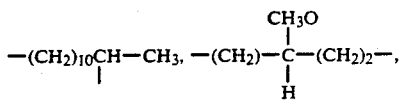
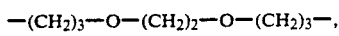
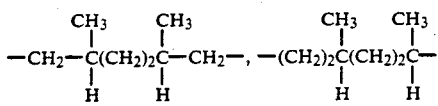
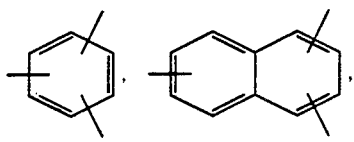
wherein R⁹ is as defined above,
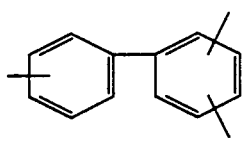
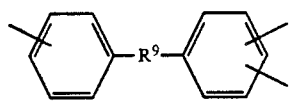
where R⁹ is as defined above
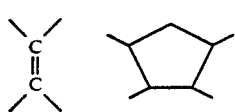
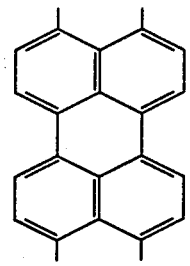
The preferable among these groups are:
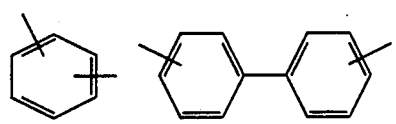
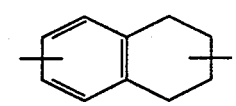
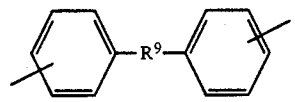
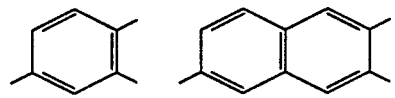
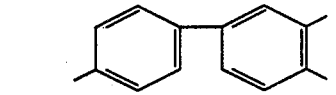
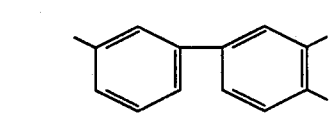
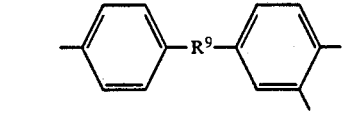
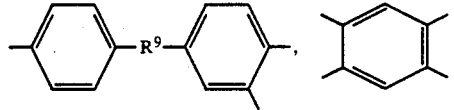
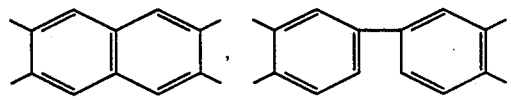
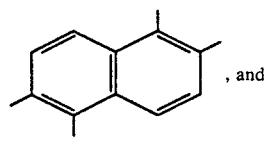, and

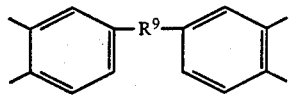

wherein R⁹ is as defined above.

Specific examples of the above-described copolymers are shown below.

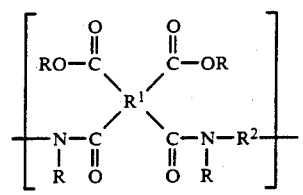

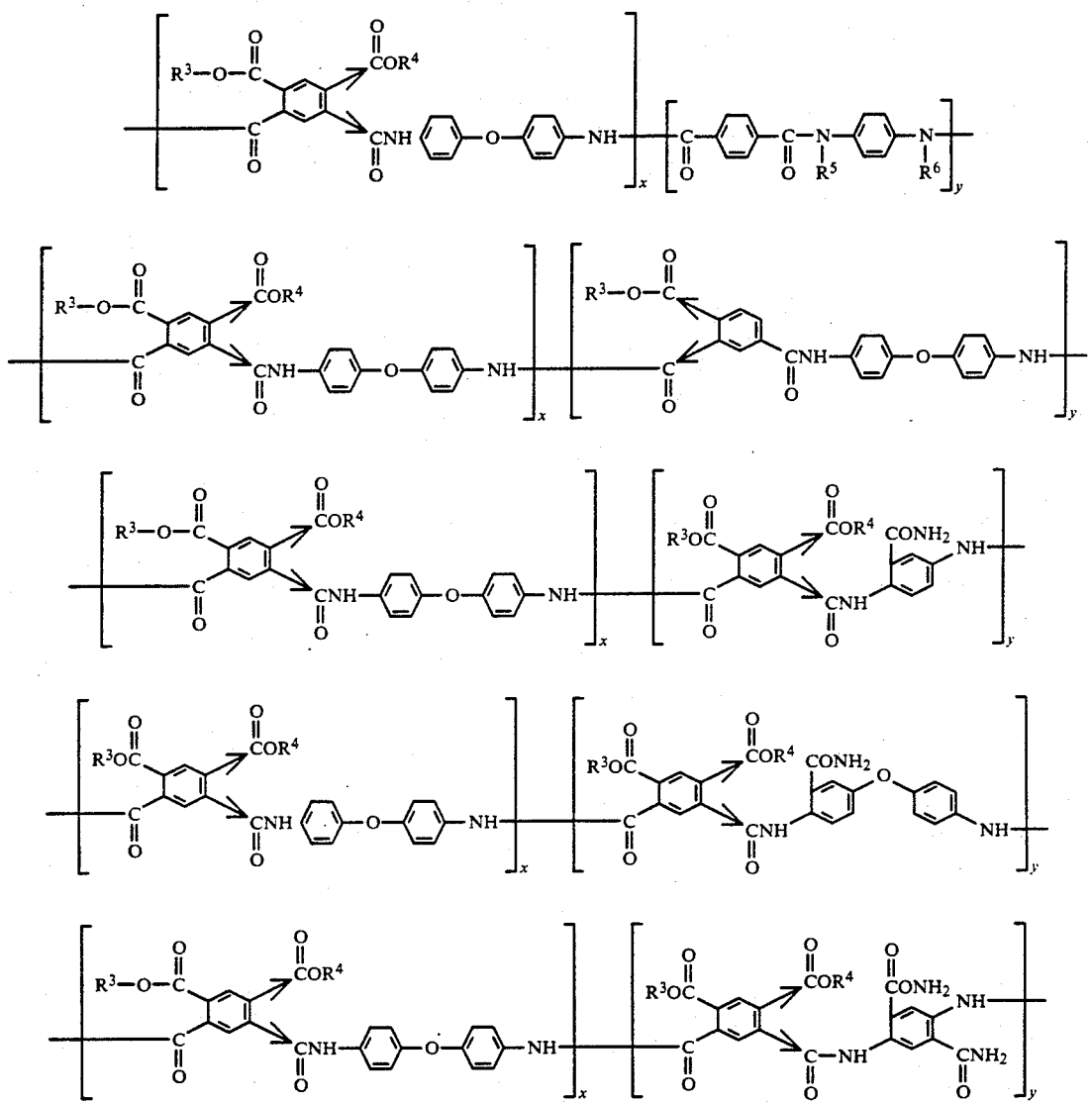

In the foregoing description concerning the recurring unit of the polyimide precursor, while at least two of $R^3$, $R^4$, $R^5$, and $R^6$ have been defined as groups other than a hydrogen atom and groups having from 1 to 11 carbon atoms, the amphiphilic polyimide precursor to be used may be copolymers containing a recurring unit represented by formula (IX) shown below in a proportion up to 30% by mole of the total recurring units.

Formula (IX) is represented by wherein $R^1$ and $R^2$ are as defined above, R is a monovalent group having 1 to 11 carbon atoms selected from the group consisting of a monovalent aliphatic group, a monovalent alicyclic group, a monovalent aromatic group, a monovalent group in which an aliphatic group is combined with an aromatic group or an alicyclic group, and their substituted monovalent groups with a halogen atom, nitro group, amino group, cyano group, methoxyl group or acetoxyl group, or hydrogen atom, and four groups R may be the same or different.

The process for preparing the amphiphilic polyimide precursor according to the present invention will be described below.

The precursor having the recurring unit represented by formula (I) can be prepared by reacting a tetracarboxylic acid dianhydride represented by formula (IV)

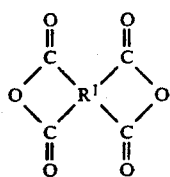   (IV)

wherein R$^1$ is as defined above, with a compound represented by formula $$R^{30}H$$

and a compound represented by formula $$R^{40}H$$

wherein R$^3$ and R$^4$ are as defined above, to obtain a compound represented by formula (V)

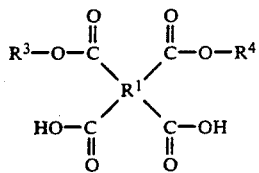   (V)

wherein R$^1$, R$^3$, and R$^4$ are as defined above, converting the compound of formula (V) to an acid halide by treating with a halide, such as thionyl chloride, phosphorous pentachloride, benzenesulfonyl chloride, etc., in a substantially water-free polar solvent at a temperature not less than $-10°$ C., and preferably about 0° C. to about 40° C., and reacting the resulting acid halide with a compound represented by formula (VI)

$$R^5-NH-R^2-NH-R^6 \quad (VI)$$

wherein R$^2$, R$^5$, and R$^6$ are as defined above, at a temperature of from $-10°$ to $+20°$ C., and preferably from 0° to $+10°$ C.

In order to complete the reaction between the acid halide and the compound of formula (VI), the reaction temperature may be raised up to 20° C. or higher after the the addition of the compound of formula (IV).

Representative examples of the compound represented by formula (IV) are:

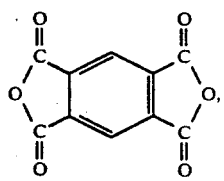

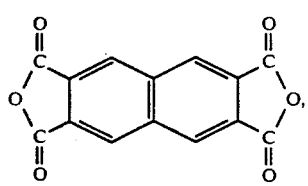

-continued

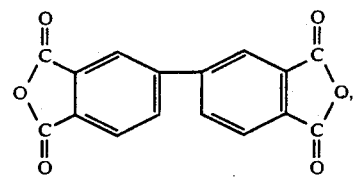

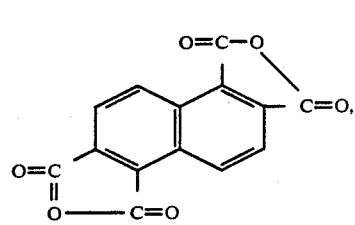

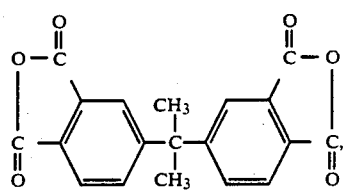

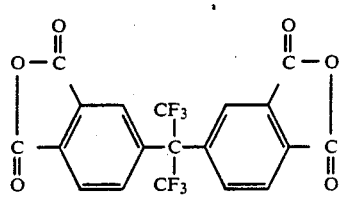

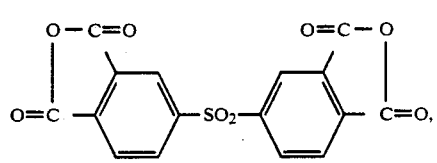

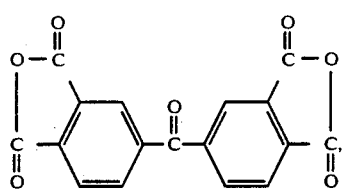

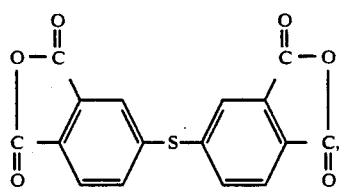

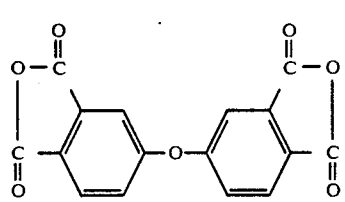

-continued

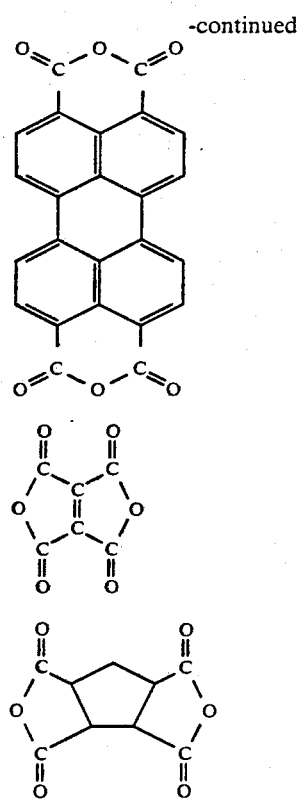

Representative examples of the compounds
$R^3OH$ and $R^4OH$ are $CH_3OH$, $CH_3CH_2OH$, $CH_3(CH_2)_2OH$, $CH_3(CH_2)_3OH$, $CH_3(CH_2)_5OH$, $CH_3(CH_2)_7OH$, $CH_3(CH_2)_9OH$, $CH_3(CH_2)_{11}OH$, $CH_3(CH_2)_{13}OH$, $CH_3(CH_2)_{15}OH$, $CH_3(CH_2)_{17}OH$, $CH_3(CH_2)_{19}OH$, $CH_3(CH_2)_{21}OH$, $CH_3(CH_2)_{23}OH$, $CF_3(CH_2)_{15}OH$, $H(CH_2)_2(CH_2)_{15}OH$, $H(CF_2)_4(CH_2)_{13}OH$, $F(CF_2)_8(CH_2)_2OH$, $F(CF_2)_8(CH_2)_4OH$,

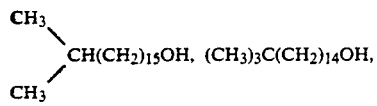

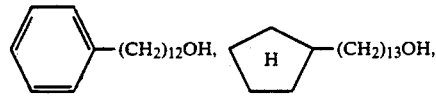

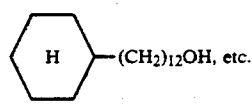

The reaction conditions for producing the compound (V) by the reaction of the tetracarboxylic acid dianhydride of formula (IV) with $R^3OH$ and $R^4OH$ are not particularly limited. For example, the reaction can be carried out at about 100° C. while stirring under a nitrogen stream for several hours, or under commonly employed conditions, such as stirring in a solvent, e.g., hexamethylphosphoramide, at room temperature for about 4 days. From the standpoint of reduction in reaction time, i.e., improvement of productivity, it is preferable that this reaction is carried out by heating at about 100° C. for 3 hours under a nitrogen stream while stirring, and, after cooling, the reaction mixture is dissolved in hexamethylphosphoramide and then subjected to the next reaction for converting into the acid halide.

The polar solvent to be used in the conversion to an acid halide includes hexamethylphosphoramide, N,N-dimethylacetamide, N,N-dimethylformamide, and the like. These solvents are used in a substantially water-free state so that the halide, such as thionyl chloride, phosphorus pentachloride, benzenesulfonyl chloride, etc., be not decomposed by moisture and the reaction proceed in the state nearly quantitatively.

If the reaction between the compound of formula (V) and the halide is conducted at a temperature lower than $-10°$ C., the reaction system becomes heterogeneous due to freezing under an influence of the long-chain alkyl group. Therefore, the reaction temperature is selected from the range of from $-10°$ C. to the vicinity of the boiling point of the produced acid halide.

The thus prepared acid halide is then reacted with the compound (VI) to produce the precursor of the present invention.

In view of workability, the thus prepared acid halide is subjected to the subsequent reaction as such without any isolation or purification procedure.

In the reaction of the acid halide and the compound (VI), both the reactants and the product tend to solidify by the long chain alkyl groups of $R^3$, $R^4$, $R^5$, $R^6$, etc., this reaction is usually carried out in a solvent, such as N,N-dimethylacetamide, N,N-dimethylformamide, etc. The reaction temperature ranges from $-10°$ to 20° C., and preferably from 0° to 10° C. If the reaction temperature is lower than $-10°$ C., the reaction system becomes heterogeneous due to freeze solidification, and if it exceeds 20° C., unfavorable side reactions are apt to take place. In order to complete the reaction, the temperature may be raised up to 20° C. or even higher after the addition of the compound of formula (VI).

Representative examples of the compound represented by formula (VI) are shown below.

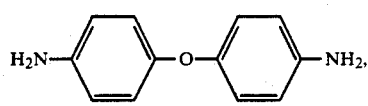

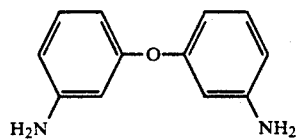

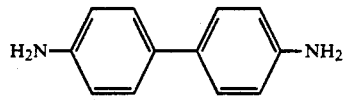

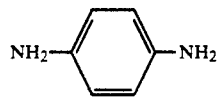

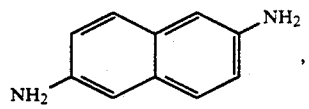

-continued

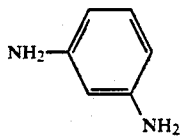

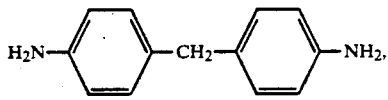

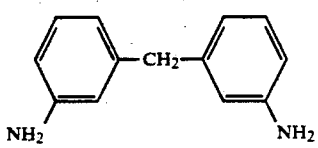

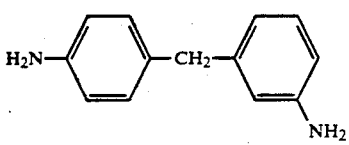

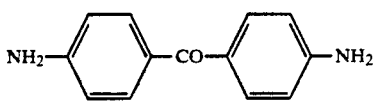

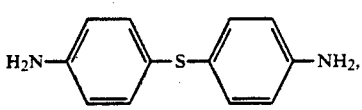

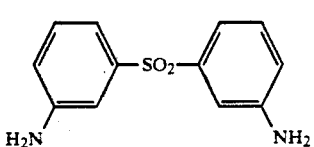

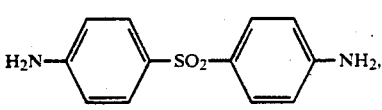

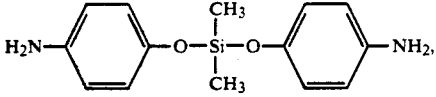

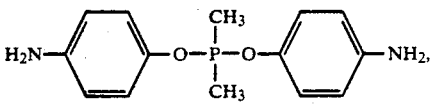

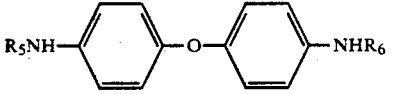

wherein $R^5$ and $R^6$ specifically include $CH_3-$, $CH_3CH_2-$, $CH_3(CH_2)_2$, $CH_3(CH_2)_3$, $CH_3(CH_2)_5$, $CH_3(CH_2)_{11}$, $CH_3(CH_2)_{13}$, $CH_3(CH_2)_{15}$, $CH_3(CH_2)_{17}$, $CH_3(CH_2)_{19}$, $CH_3(CH_2)_{21}$, $CH_3(CH_2)_{23}$, $CF_3(CH_2)_{15}$, $H(CF_2)_2(CH_2)_{15}$, $H(CF_2)_4(CH_2)_{13}$, $F(CF_2)_8(CH_2)_2$, $F(CF_2)_8(CH_2)_4$, etc.

The ratio of the acid halide to the compound of formula (VI) is appropriately selected so as to produce the precursor having a desired molecular weight, and usually ranges from 1/0.8 to 1/1.2 by mole. In order to obtain the precursor having a high molecular weight, it is preferable to use stoichiometric amounts of purified monomers and purified solvents.

When each of $R^3$ in $R^3OH$ and $R^4$ in $R^4OH$ does not represent a hydrogen atom or a group having from 1 to 11 carbon atoms, both $R^5$ and $R^6$ in the compound of formula (VI) may be hydrogen atoms. In this case, the precursor having the recurring unit of formula (II) can be obtained.

The use of the compound (VI) wherein both $R^5$ and $R^6$ are hydrogen atoms is advantageous in that the reactivity is good and the raw material cost is unexpensive. Further, since the precursor obtained therefrom is thermally stable owing to the carboxylic acid moiety in the form of an ester and can be isolated as a solid powder without undergoing further reaction when dried. Moreover, the product is easy to purify.

The precursor having the recurring unit of formula (I) wherein both $R^4$ and $R^3$ are hydrogen atoms, i.e., the recurring unit represented by formula (III), can also be prepared by directly reacting the tetracarboxylic acid dianhydride of formula (IV) with a compound represented by formula (VII)

$$R^7-NH-R^2-NH-R^8 \qquad (VII)$$

wherein $R^7$ and $R^8$ are as defined above.

Representative examples of the compound represented by formula (VII) are shown below.

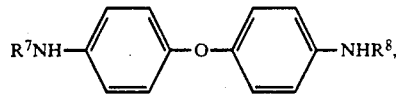

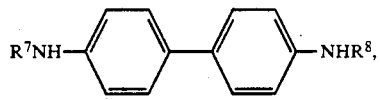

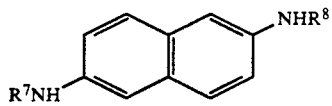

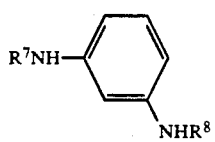

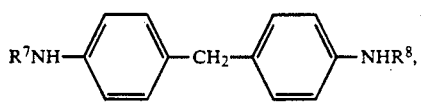

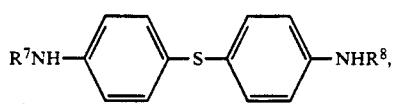

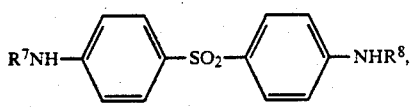

wherein $R^7$ and $R^8$ specifically include $CH_3(CH_2)_{n-1}$, (n=12 to 30), $CH_3(CH_2)_{15}$, $H(CF_2)_2(CH_2)_{15}$, $H(CF_2)_4(CH_2)_{13}$, $F(CF_2)_8(CH_2)_2$, $H(CF_2)_8(CH_2)_4$, etc.

The reaction between the tetracarboxylic acid dianhydride of formula (IV) and the compound of formula (VII) can be carried out under the conditions employed for the preparation of ordinary polyamic acids. For example, the reaction is effected in a substantialy water-free organic polar solvent at a temperature of not higher than 50° C., and preferably at room temperature. The compound of formula (VII) is used in an amount of from 0.8 to 1.2 mol per mol of the tetracarboxylic acid dianhydride of formula (IV).

The thus obtained polyimide precursor having the recurring unit represented by formula (III) is characterized in that it is easily prepared as described above and that it can be formed in a film by the LB process, which is then heated to provide a polyimide film.

The above-described copolymers can also be prepared in the same manner as described above for the amphiphilic polyimide precursors.

LB films can be formed from the precursors of the present invention by any of the so-called LB technique without restriction, e.g., the vertical dipping method (LB method), the horizontal dipping method, the revolving cylindrical method and so on (as described in Shin Jikken Kagaku Koza, Vol. 18, "Interface and Colloid", pages 498–508). The LB technique is a method in which a LB material is spread onto the surface of water and compressed at a constant surface pressure to form monomolecular layer film and the monomolecular layer is transferred onto a substrate.

In general, spreading of an LB film-forming substance on the surface of water is effected by using a solution of the substance in a solvent which is water-insoluble and is evaporated in a gaseous phase, such as benzene, chloroform, etc. In the preparation of a spreading solution of the precursor according to the present invention, an organic polar solvent is preferably used in combination in order to increase solubility of the precursor. Such an organic polar solvent includes N,N-dimethylformamide, N,N-dimethylacetamide, N,N-diethylformamide, N,N-diethylacetamide, N,N-dimethylmethoxyacetamide, dimethyl sulfoxide, N-methyl-2-pyrrolidone, pyridine, dimethylsulfone, hexamethylphosphormaide, tetramethylenesulfone, dimethyltetramethylenesulfone, etc.

When the precursor dissolved in a combination of benzene, chloroform, etc. and the above-described organic polar solvent is spread on the surface of water, it appears that benzene, chloroform, etc. is evaporated in a gaseous phase while the organic polar solvent is dissolved in a large amount of water.

The concentration of the precursor solution to be spread on the surface of water is not particularly limited, but usually ranges from about 2 to $5 \times 10^{-3}$M. Addition of a metal ion to the solution or pH adjustment of the solution is not always required for obtaining satisfactory film-forming properties. Elimination of metal ions rather seems advantageous for use in the field of electronics.

In a preferred embodiment for building up the polyimide precursor of the present invention on a substrate, use of a mixture of the precursor of the invention and known LB film-forming compounds brings about an improvement on film-forming properties as previously proposed by the present inventors.

The LB film-forming compounds which can be used in combination are well known in the art and described, e.g., in the above-cited references. Preferred among them are compounds containing a hydrocarbon group having from about 16 to about 22 carbon atoms and a hydrophilic group, such as those of formulas

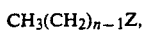

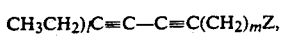

wherein n represents an integer of from 16 to 22; $l+m=n-5$; and Z represents OH, $NH_2$, COOH, $CONH_2$, or COOR', wherein R' represents a lower aliphatic hydrocarbon group.

From considerations of improved film-forming properties, the compounds of formula $CH_3(CH_2)_{n-1}Z$ are advantageous in cost. On the other hand, those containing an unsaturated bond are polymerizable upon exposure to light or radiation.

The mixing ratio of at least one of these LB film-forming compounds and the precursor of the invention is not particularly limited. Further, two or more compounds selected from the polyimide precursors and copolymers according to the present invention may also be used as a mixture.

The substrate on which LB films are formed is not particularly restricted and can be selected appropriately depending on the end use of the film. It should be noted, however, that the substrate is required to be heat resistant when the LB film thereon is heated for imidation.

Examples of the substrate to be used include inorganic substrates made of glass, alumina, quartz, etc.; plastic substrates; inorganic or plastic plates on which a metal thin film is deposited; metal-made substrates; substrates of semiconductors of the Groups VI, III-V, II-VI, etc. of the Periodic Table, e.g., Si, GaAs, ZnS, etc.; substrates made of ferroelectric substance, e.g., $PbTiO_3$, $BaTiO_3$, $LiNbO_3$, $LiTaO_3$, etc.; substrates made of magnetic substances; and the like.

The aforesaid metal thin film on the substrate may have a pattern suited for the particular application. The substrate made of a semiconductor such as Si, GaAs, ZnS, etc. or a ferroelectric substance may be processed beforehand to form devices. If desired, any of the above-enumerated substrates may be subjected to surface treatment commonly employed in the art.

Since the polyimide precursors according to the present invention show a tendency of weak adhesion to glass, quartz, silicon, silicon dioxide, and the like, it is desirable to improve film-forming properties and adhesion by treating such a substrate with a silane coupling agent, and particularly a silane coupling agent having an amino group or an epoxy group and an alkoxy group, such as A-1100 or A-187 produced by UCC, or with a chelate containing aluminum to form an alumina layer. It is also possible, as is usual in the art, to form a few or several layers of a higher fatty acid metal salt on the substrate.

By the use of the precursors of the present invention, a thin film excellent in heat resistance, mechanical characteristics, chemical resistance and electric insulation properties can be formed on a substrate according to the LB process Imidation of the resulting film provides a thin film having further enhanced heat resistance.

The process for imidation is not particularly limited, but imidation is generally carried out by heating at a temperature in the vicinity of 200° to 400° C. A laser beam may also be used for imidation. It may also be effected by the use of acetic anhydride or pyridine commonly employed for imidizing polyamic acids either alone or in combination with the thermal reaction.

Taking the recurring unit of formula (II) or (III) for instance, the imidation reaction proceeds as illustrated below.

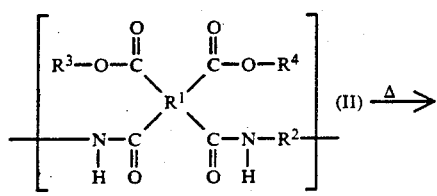

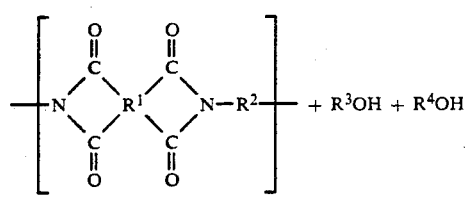

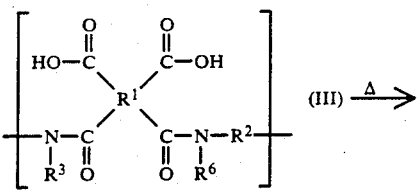

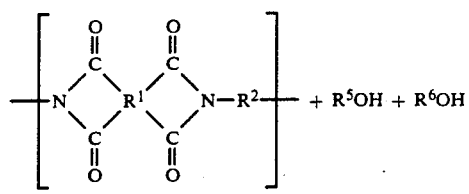

Although the polyamic acid unit represented by formula (VIII) is also imidized to form a polyimide while forming $H_2O$, such a polyimide cannot be utilized as an LB film. The copolymers according to the present invention, in which a part of $R^1$ and/or $R^2$ is replaced with a group having a different valence, also undergo reaction as illustrated below under the same conditions as described above.

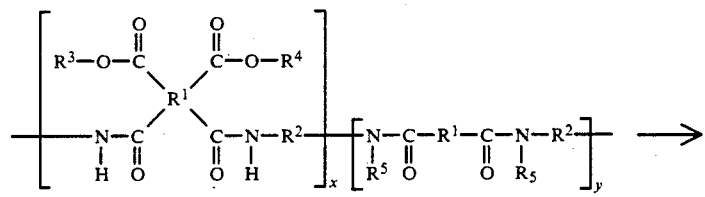

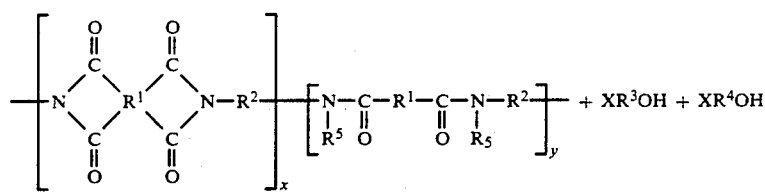

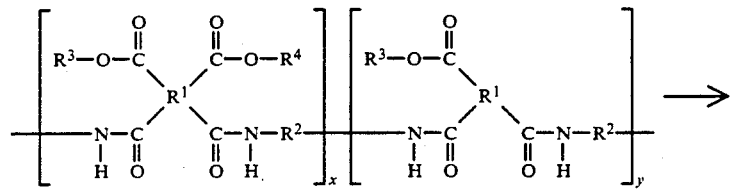

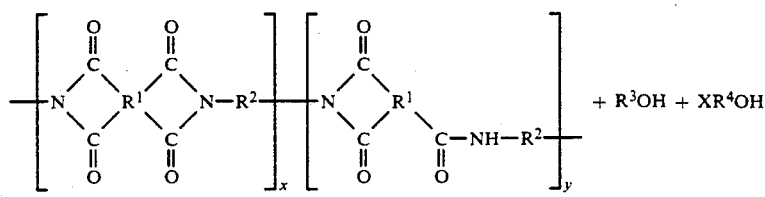

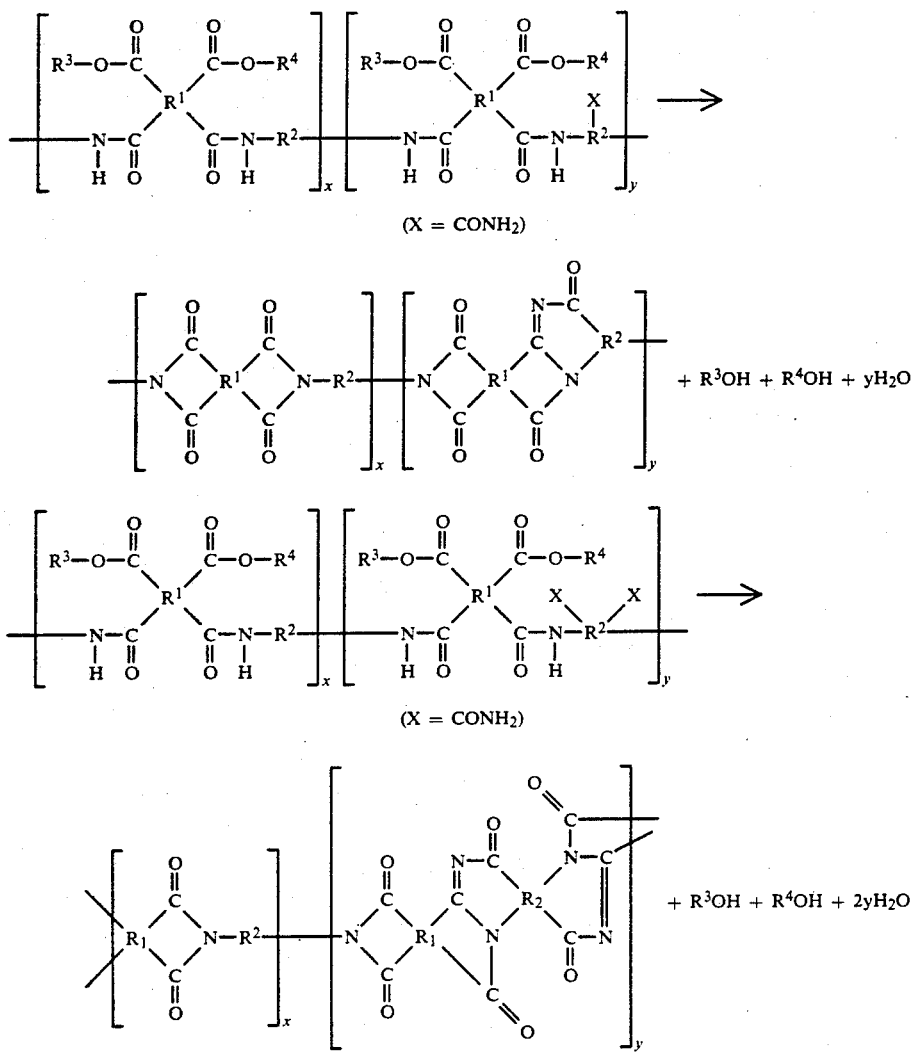

In particular, the last two of the above-illustrated reactions are advantageous in that a highly heat-resistant skeleton can be introduced to thereby assure heat resistance of the polyimide films.

As shown in the above-described reaction schemes, the imidation reaction or other cyclization reaction is accompanied by release of the groups having been introduced for rendering the precursor hydrophobic in the form of an alcohol. Since the thus released alcohol can be evaporated at a temperature in the vicinity of from 200° to 400° C., if desired, under a gas stream or in vacuo, a polyimide thin film having high heat resistance and excellent insulating properties can be obtained.

Further, the known LB film-forming compound to be added for improving film-forming properties can be selected from those which can be evaporated under the conditions for the imidation reaction or other cyclization reaction so as to obtain a polyimide thin film having high heat resistance and electric insulation properties.

As described above, the polyimide thin film obtained by building up the amphiphilic polyimide precursor on a substrate by the LB process followed by imidation is excellent in heat resistance, mechanical characteristics, chemical resistance, and electric insulation properties. Moreover, the polyimide thin film is very thin as having a thickness of 10000 Å or smaller, e.g., 5000 Å or 2000 Å. If desired, it is possible to form a film having a thickness further reduced to 10 to 1000 Å. In particular, the polyimide thin film exhibits satisfactory physical properties, inter alia, excellent insulating properties as having a dielectric breakdown strength of $1 \times 10^6$ V/cm or more, even with a thickness of not more than 1000 Å, e.g., several hundreds of angstroms or even smaller, e.g., about 50 to 100 Å, it can be applied to a wide variety of electric-electronic devices. Thin films of from about 50 Å to several hundreds of angstroms are particularly expected to exert specific effects ascribed to the small film thickness, such as a tunnel effect, and many interesting applications taking advantage of such an effect would be realized.

The electric-electronic devices including the polyimide thin film in accordance with the present invention will be described below.

Devices of the first importance including the polyimide thin film have a metal/insulating film/semi-conductor structure (hereinafter referred to as MIS structure), which provides bases of planar electronic devices or integrated circuits.

FIGS. 1 to 7 each illustrates a schematic view of a typical MIS structure. The structure of FIG. 1 comprises a semiconductor substrate (S), an insulating film (I) which is a polyimide thin film, and metal electrode (M) formed in this order. The semi conductors to be used include those of the Group IV of the Periodic Table, e.g., Si, Ge, etc.; those of the group III-V, e.g., GaAs, GaP, InP, etc.; and those of Group II-IV, e.g., CdTe, CdS, ZnS, ZnSe, CdHgTe, etc. The MIS structure using these semi conductors can construct various semiconductor devices, such as photoelectric elements, such as solar cells; light-emitting devices, such as light-emitting diodes (LED), EL, photodiodes, etc.; light-receiving devices; light-detecting device; and various transducers, such as gas sensors, temperature sensors, etc. The semiconductor to be used may have any of a single crystal form, a polycrystalline form, and an amorphous form.

Figure 2:
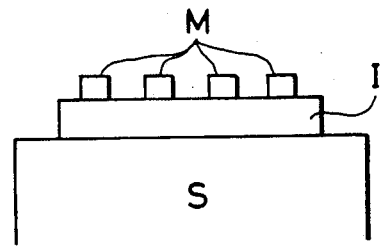

FIG. 2 also illustrates an MIS structure, in which two or more elements are formed on a substrate, which is of interest for application to charge-transport type devices, such as charge-coupled devices (CCD).

Figure 3:
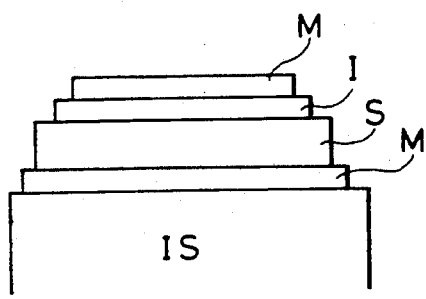
Figure 4:
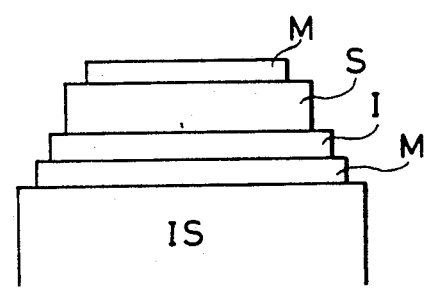

FIG. 3 illustrates a structure, in which an insulating substrate (IS) having an electrode (M), which may be a transparent electrode or may be patterned, has provided thereon a semi-conductor (S) in the form of, in many cases, a thin film, and further provided thereon a polyimide thin film (I) and an electrode (M) in this order. FIG. 4 is the same as FIG. 3 except that the polyimide thin film (I) is provided between the electrode (M) on the IS side and the semiconductor film (S).

The semiconductor thin film can be prepared by any conventional processes, such as molecular beam epitaxy (MBE), metal organic compound vapor deposition (MOCVD), atomic layer epitaxy (ALE) vacuum evaporation, sputtering, spray pyrolysis, coating, and the like.

The semiconductor to be used in the structures of FIGS. 3 and 4 can be selected from the same examples enumerated for the structures of FIGS. 1 and 2, and the devices to which these structure are applicable are the same as for FIGS. 1 and 2.

According to the structure of FIG. 4 in which the semiconductor thin film is formed on the polyimide thin film, it is not favorable that the heat for the semiconductor thin film formation exceeds heat-resistance of the polyimide thin film. In this connection, amorphous silicon or the like can be built up sufficiently. With respect to other semiconductors, the recent and future advancements in techniques of low-temperature film formation would broaden the range of semiconductors usable.

Figure 5:
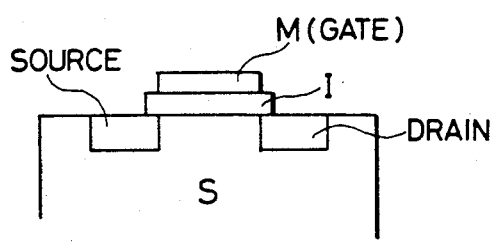
Figure 6:
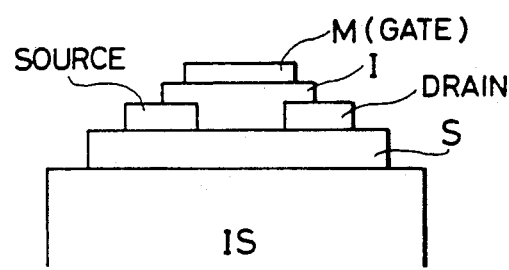

The most important structures of the MIS structure devices are so-called field effect transistor (FET) structures that are driven by controlling a channel current by gate electrodes as typically shown in FIGS. 5 and 6. The structure of FIG. 5 uses a semiconductor substrate (S) while that of FIG. 6 uses an insulating substance (IS) on which a semiconductor is formed usually in the form of a thin film.

The MIS FET structure is one of basic device forms, by which various devices can be constructed. For example, thin film transistors for driving liquid crystal displays can be obtained by constructing this structure on a substrate of a large area, and integrated circuits can be obtained by increasing the degree of integration.

Other interesting applications are structures of FIGS. 5 and 6 from which the gate electrodes are removed. To this structure is fixed an insulating film either alone or in combination with a membrane sensitive to ions, gases or active substances to construct an ion-sensitive FET (ISFET), a gas-sensitive FET (Chem FET), an immuno FET (IMFET), or an enzyme FET (ENFET).

The operation principle can be accounted for by the field effect through the action of ions, gases or active substances upon the surface of the gate insulating film. The polyimide thin film of the present invention is advantageous as compared with the conventional inorganic substances when the thin film is further modified with various organic substances.

Figure 7:
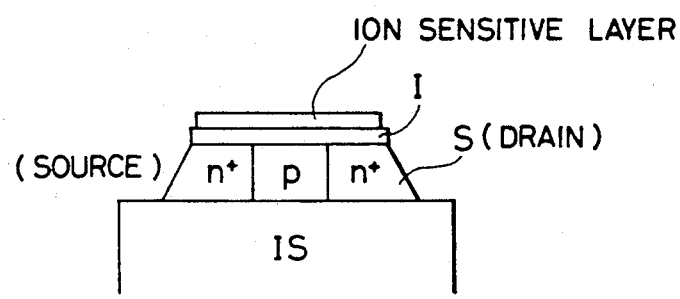

FIG. 7 illustrates an example of ISFET, in which a silicon semiconductor film is formed on a quartz substrate (IS) in such a manner as shown in the figure and an insulating film and an ion-sensitive film are provided thereon. The polyimide thin film according to the present invention can be used as the insulating film in this structure.

In a preferred embodiment of this invention, the semiconductors for constructing devices having an MIS structure are those of compounds of the Groups III-V, II-IV, etc. that are generally difficult to be formed in films having satisfactory insulating properties by oxidation or the like technique. For instance, the conventional devices using GaAs as a semiconductor have been practically employed in the form of metal-semiconductor FET (MESFET) in the light of the above-described problem. To the contrary, it is expected by the present invention to improve performance properties by adopting the MIS structure.

When an MIS integrated circuit is constructed by using GaAs, an effect to decrease an operating voltage can be produced In addition, an integral circuit operating at a high electron mobility (HEMT) taking advantage of high carrier mobility in the GaAs semi conductor can be produced through a very simple process.

Figure 8:
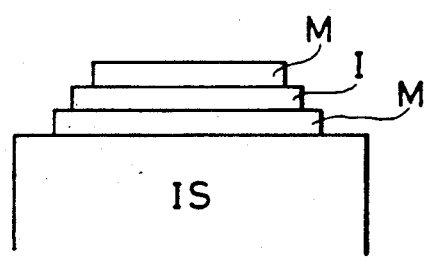
Figure 9:
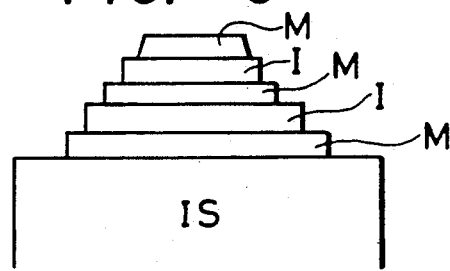
Figure 10:
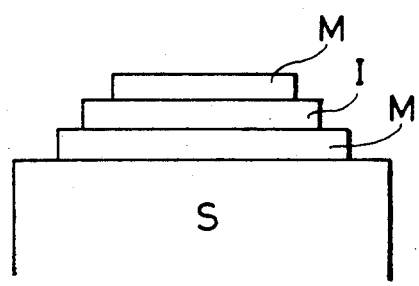

Devices of the second importance including the polyimide thin film according to the present invention have a metal/insulating film/metal structure (hereinafter referred to as MIM structure). FIGS. 8 to 10 each illustrates a schematic view of the MIM structure, in which a metal, an insulating film, and a metal are formed on an insulating substrate (IS) or a semiconductor substrate (S) in this order.

FIG. 8 illustrates a structure of a capacitor. The capacitor of this structure may also serve as a humidity sensor by tracing changes in capacitance with humidity. Transistors having an MIM structure can be produced in accordance with this structure.

FIG. 9 illustrates an MIM structure when applied to a hot electron transistor.

FIG. 10 illustrates a structure applicable to a capacitor for a memory cell of VLSI, in which a capacitor is formed on a semiconductor or a semi conductor device. This structure is also applied to devices in which hot electrons are injected into a semiconductors. Further, the metal can be replaced with superconductor, e.g., Nb, to produce a Josephson junction device (JJ).

Figure 11:
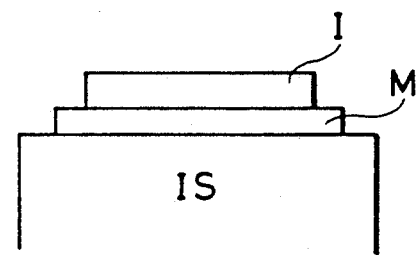
Figure 12:
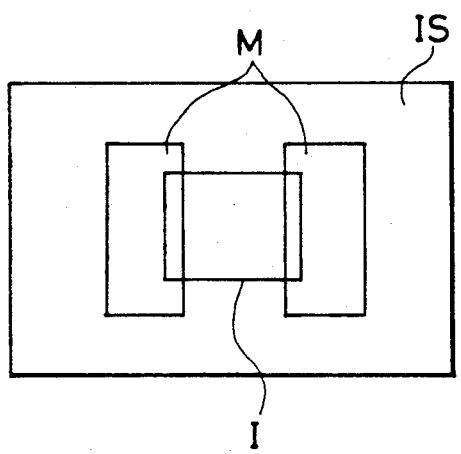
Figure 13:
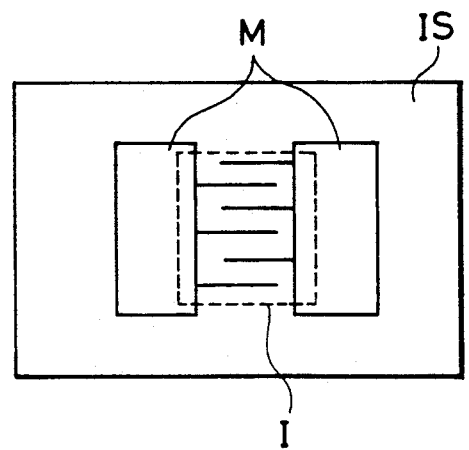

The devices of third importance containing the polyimide thin film of the present invention have an insulating film/metal structure (hereinafter referred to as IM structure) as schematically shown in FIG. 11. This is the simplest structure obtained by forming a polyimide thin film as an insulating film on a metal layer. One of the applications is a liquid crystal oriented film, that is obtained by forming a polyimide film on a patterned electrode, usually a transparent electrode, e.g., ITO. Other applications are sensors for humidity, gases, etc.

as shown in FIGS. 12 and 13, wherein a polyimide film is formed on two independent electrodes.

Other applications of the polyimide thin films of this invention in addition to the aforesaid devices are described in the above-cited literature, and particularly P. S. Vincett and G. G. Roberts, *Thin Solid Films*, Vol. 68, pp.135–171 (1980).

With respect to other semi-conductor devices and compound semi-conductor devices, E. S. Yang, *Fundamentals of Semiconductor Devices*, Magraw-Hill (1978) and Imai, et al. (ed.), *Kagobutsu Handotai Device* (I) & (II), Kogyo Chosakai (1984) can be referred to.

The process for producing the amphiphilic polyimide precursor of the present invention, the process for forming the film and an electric and electronic device of the present invention will be explained hereinbelow by way of examples, but the present invention is not deemed to be limited thereto.

EXAMPLE 1

In a flask was reacted with 2.18 g (0.01 mol) of pyromellitic acid anhydride with 5.40 g (0.02 mol) of stearyl alcohol at ca. 100° C. in for 3 hours a stream of dry nitrogen.

The thus obtained product was dissolved in 40 ml of hexamethylphosphoramide and cooled to 0 to 5° C. Then 2.38 g of thionyl chloride was added dropwise to the reaction mixture at ca. 5° C., and the resulting mixture was maintained at the same temperature for 1 hour to allow the reaction to complete.

Thereafter, a solution of 2 g (0.01 mol) of diaminodiphenyl ether in 50 ml of dimethylacetamide was added dropwise to the reaction mixture under a temperature of from 0° to 5° C., and the reaction was allowed to continue for ca. 1 hour after the completion of the dropping. The reaction mixture was then poured into 600 ml of distilled water to precipitate the product. The precipitate formed was filtered and dried at 40° C. to give ca. 9 g of light yellow powders.

The thus obtained product was analyzed by IR spectrometry, thermogravimetric analysis (TGA) and differential thermal analysis (DTA), and its molecular weight was measured by the GPC method. The following results were obtained.

IR Spectrometry

Figure 14:
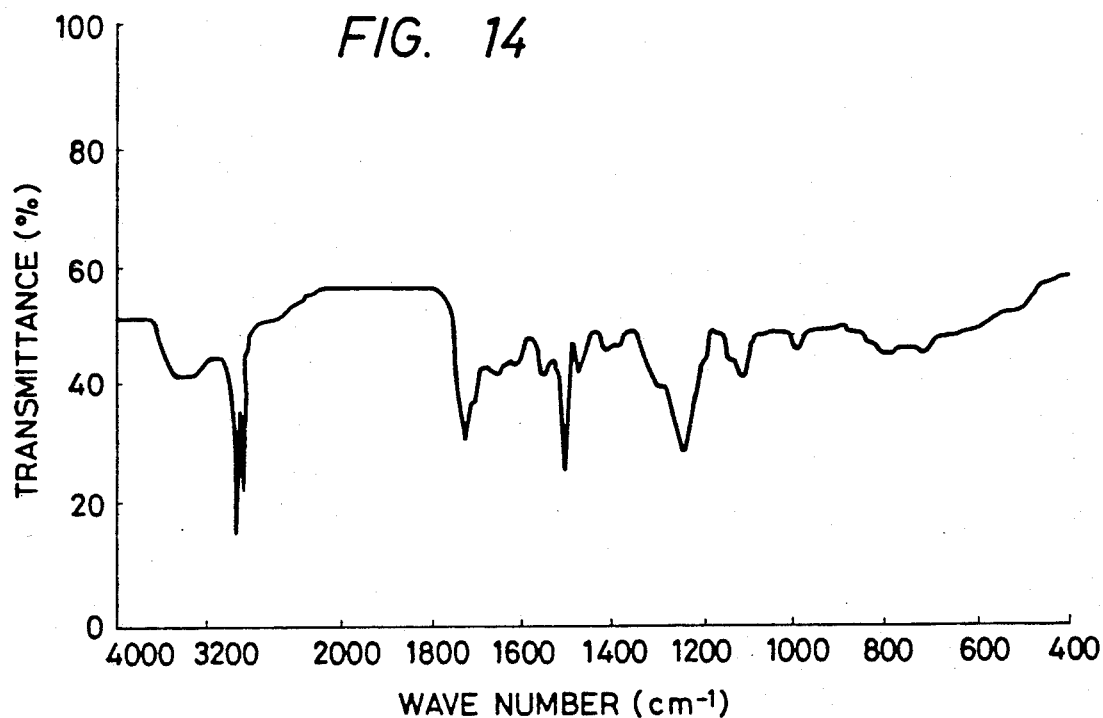
FIGS. 14 shows an IR spectrum of the precursor obtained in Example 1.

The IR chart shown in FIG. 14 was obtained by the KBr disc method. Absorption peaks characteristic of esters, amides I, II and III, alkyl chains and ethers are observed in the chart.

Thermal Analysis (TGA-DTA)

Figure 15:
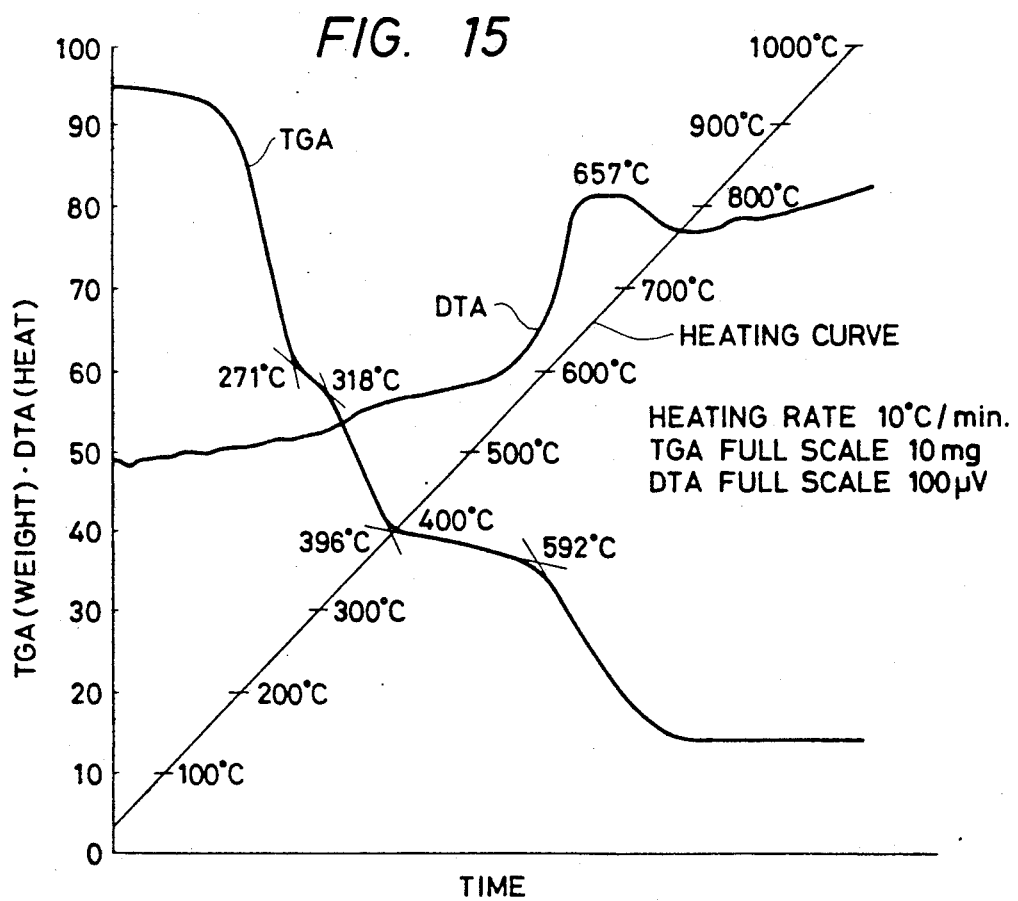
FIG. 15 is a graph showing the results of thermogravimetric analysis (TGA-DTA) for the precursor obtained in Example 1.

The thermal properties of the product were measured in a nitrogen stream by using an RTG-DTA of type (H) manufactured by Rigaku Densi Co., Ltd., under the following conditions: TGA full scale, 10 mg; DTA full scale, 100 μV; maximum temperature, 1,000° C., and rate of heating 10° C./min, and the results shown in FIG. 15 were obtained. In the TGA are observed inflection points at 271°, 318°, 396° and 592° C. In the DTA is observed a characteristic peak at around 657° C.

Figure 16:
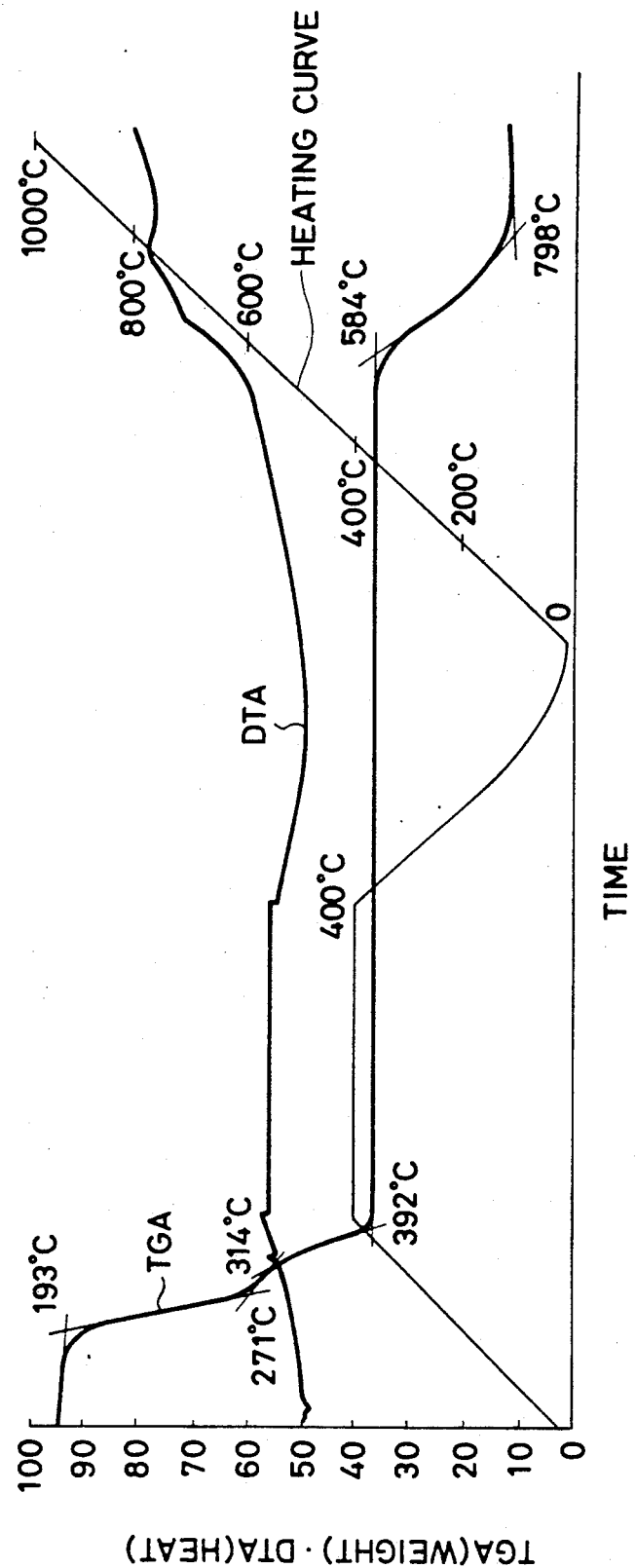
FIG. 16 is a graph showing the results of thermogravimetric analysis for the precursor obtained in Example 1, wherein the precursor is heated from room temperature to 400° C, held at that temperature for 1 hour, cooled down to room temperature, and then heated up to 1000° C.

On the other hand, FIG. 16 shows TGA and DTA curves obtained at the time when a sample of the precursor was heated up to 400° C. at a heating rate of 10° C./min, maintained at the same temperature for 1 hour, cooled to room temperature, and then heated again up to 1,000° C. at a heating rate of 10° C./min When maintained at 400° C. for 1 hour, the sample attained at almost constant weight, that is to say, the imidation reaction was completed. When the sample was cooled to room temperature, and then reheated, it showed no change in its weight up to temperature exceeding 450° C., and its thermal decomposition started at 584° C., which is identical with the thermal decomposition temperature of corresponding commercial polyimide films. Accordingly, it can be said that a product having a heat resistance comparable to that of polyimide films could be obtained by completing the imidation.

Measurement of Molecular Weight by GPC

A number average molecular weight of ca. 50,000 (reduced to polystyrene) was obtained by GPC measured in N,N-dimethylformamide.

EXAMPLE 2

In an 8:2 mixture (by volume) of distilled chloroform and distilled dimethylformamide was dissolved 55.1 mg of the product obtained in Example 1 to prepare 25 ml of LB film spreading solution.

Figure 17:
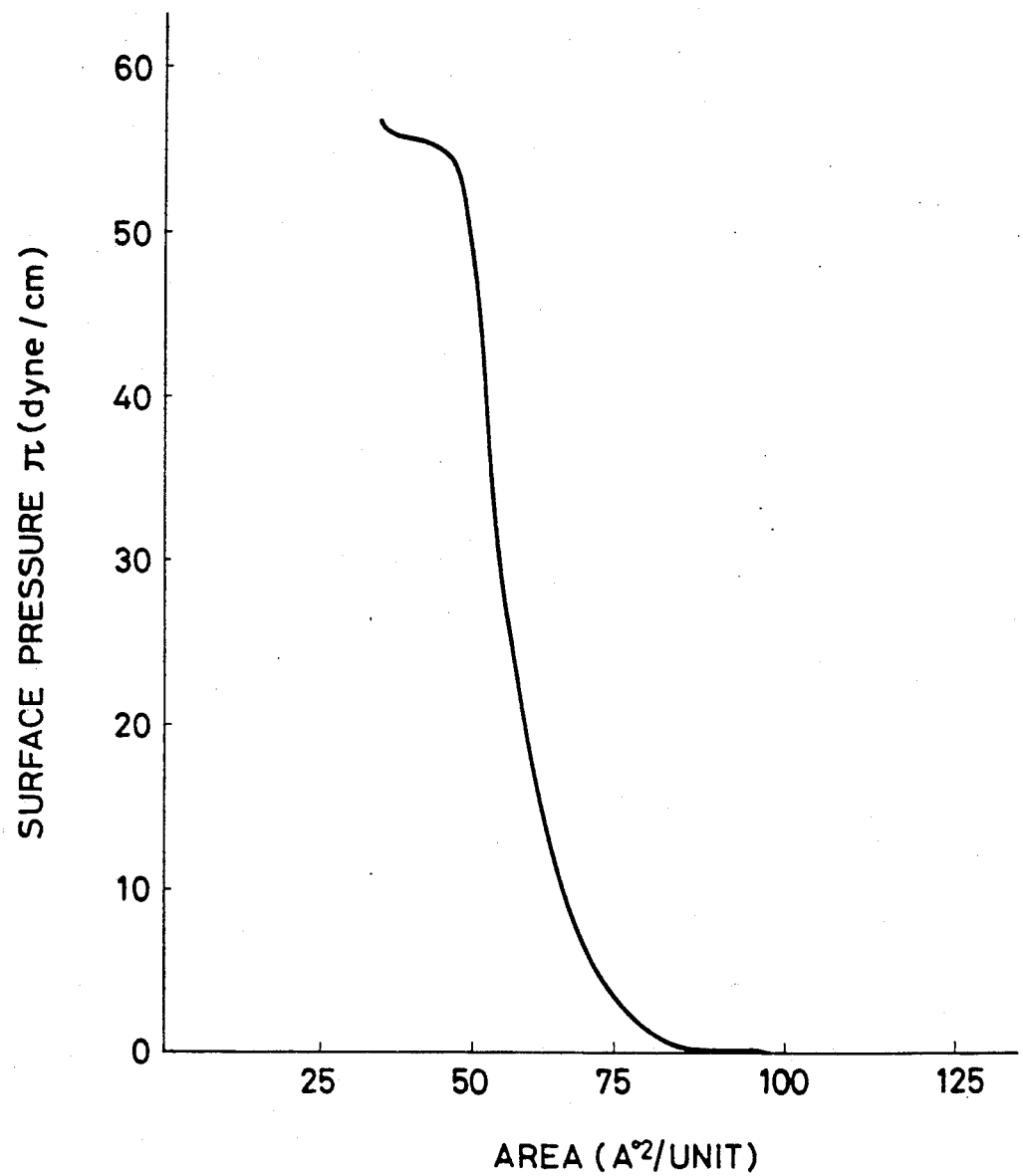
FIG. 17 is a graph showing the relationship between a surface pressure and an area per recurring unit of the precursor obtained in Example 1 when spreaded on the surface of water.

The relationship between surface pressure (x) and area per recurring unit was measured on the surface of redistilled water, and the results shown in FIG. 17 was obtained. The surface pressure rose steeply at around 75 $Å^2$/unit, and a good condensed films was formed. Its limiting area was 60 $Å^2$/unit, and its collapse pressure was 55 dyne/cm, which is extremely as high as a polymeric LB film. When the film was held on the surface of water, maintaining its surface pressure at 25 dyne/cm, its surface area showed no decrease over a period of two hours and the film remained stable.

Figure 18:
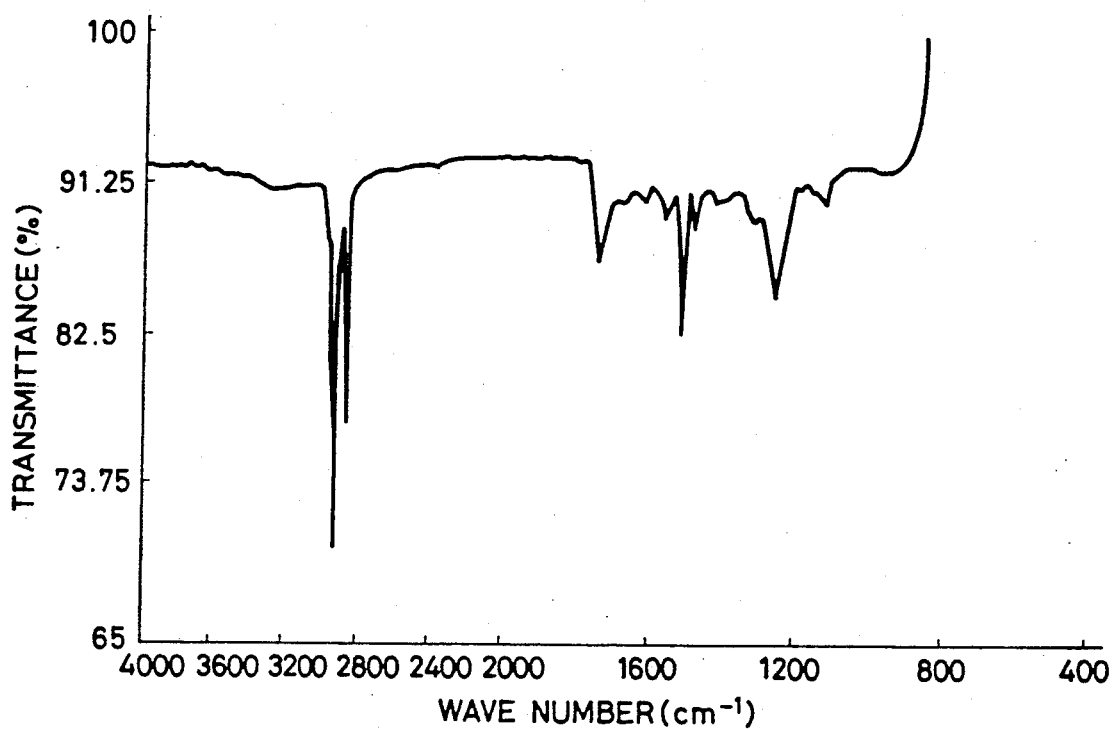
FIG. 18 is a spectrum showing the results of FT-IR for the film obtained by spreading the precursor obtained in Example 1 on the surface of water and depositing on a $CaF_2$ substrate by an LB technique.

The film was transferred onto a glass plate or a $CaF_2$ plate by Langmuir-Blodgett technique at a dipping speed of 10 mm/min, thereby maintaining the surface pressure at 25 dyne/cm. 90 Layers were deposited on the plate. The multilayer films built up or deposited on the $CaF_2$ plate gave an FT-IR shown in FIG. 18, which is identical with that of the product obtained in Example 1. It was also confirmed by X-ray diffraction that the deposited 90 layers film consisting of Y-type layers, only one peak was observed at $2\theta = 4.65°$ in spite of the fact that the film did not contain $Cd^{++}$ or the like.

When n is 3, and λ is 1.5418 Å under Bragg's diffraction condition of $n\theta$ being $2d.\sin\theta$, a thickness of monolayer film is calculated as 28.5 Å. The result is considered as being almost in conformity with a value provided that a long chain alkyl groups in amphiphilic polyimide precursor stands vertically.

It was confirmed by the peaks at 1790 and 1710 $cm^{-1}$ in its FT-ATR-IR analysis that $\alpha,\beta$-unsaturated 5-membered imide rings were formed when the deposited film were heated at 400° C. for 1 hour.

It was also confirmed by IR spectrometry that imidation took place when the product obtained in Example 1 was heated at 400° C. for 1 hour, thereby decreasing its weight by 58% by weight, which is well in conformity with the theoretical value of 58.7% calculated with the assumption that stearyl alcohol was eliminated by the imidation.

COMPARATIVE EXAMPLE 1

Figure 19:
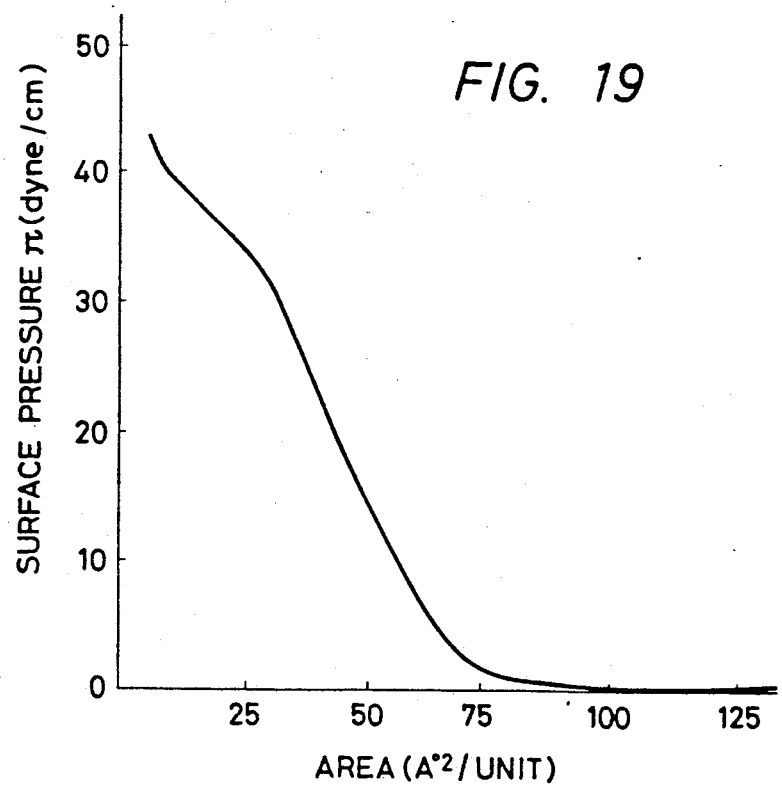
FIG. 19 is a graph showing the relationship between a surface pressure and an area per recurring unit of the precursor obtained in Comparative Example 1.

A polyimide precursor was synthesized in the same manner as in Example 1, except that n-decyl alcohol (n-$C_{10}H_{21}OH$) was used instead of stearyl alcohol. As far as IR spectrum, thermal analysis and molecular weight measured by GPC are concerned, the polyimide precursor showed the same characteristics as those of the polyimide obtained in Example 1. However, the surface pressure-area curve of the precursor, shown in FIG. 19, indicates the presence of a liquid expansion phase and denies the existence of a condensed phase. It would, therefore, be apparent that an alkyl group containing only 10 carbon atoms would be too short to give a polymer capable of forming a stable condensed film.

EXAMPLES 3-5

Example 1 was repeated to synthesize a polyimide precursor, except that lauryl alcohol (containing 12 carbon atoms), myristyl alcohol (containing 14 carbon atoms) or cetyl alcohol (containing 16 carbon atoms) were used instead of stearyl alcohol. In cases where alcohols containing 12 to 14 carbon atoms were used, there were obtained products showing characteristics between those of the products prepared from $C_{10}$ and $C_{18}$ alcohols and a stable condensed phase was obtained where a water phase was cooled to around 5° C. In the case where the $C_{16}$ alcohol was used, there was obtained a product capable of forming a condensed film which was as stable as in the case of $C_{18}$.

EXAMPLE 6

10.91 g of pyrromellitic acid dianhydride was reacted with 27.05 g of stearyl alcohol at 120° C. for 3 hours. The product obtained was recrystallized from 200 ml of ethanol to give distearyl pyrromellitate having a melting point of 133°-137° C. 3.79 g of this distearyl pyrromellitate was dissolved in 60 cc of hexamethylphosphoramide and cooled to 5° C., and then 1.19 g of thionyl chloride was dropwise added thereto at about 5° C. By allowing the solution to stand for about one hour after dropping, the reaction was completed. Subsequently, 1.2 g of diaminodiphenyl ether dissolved in 30 cc of dimethylacetamide was dropwise added at about 10° C., and after reaction was conducted for two hours by elevating the reaction temperature to about 20° C., the reaction mixture was poured in 400 cc of ethanol to precipitate the reaction product, which was filtered and dried at 40° C., whereby ca. 3.4 g of pale yellow powder was obtained.

The results of the measurement of molecular weight by IR spectrum analysis, thermal analysis (TGA-DTA) and GPC were as follows.

IR Spectrum Analysis

Figure 20:
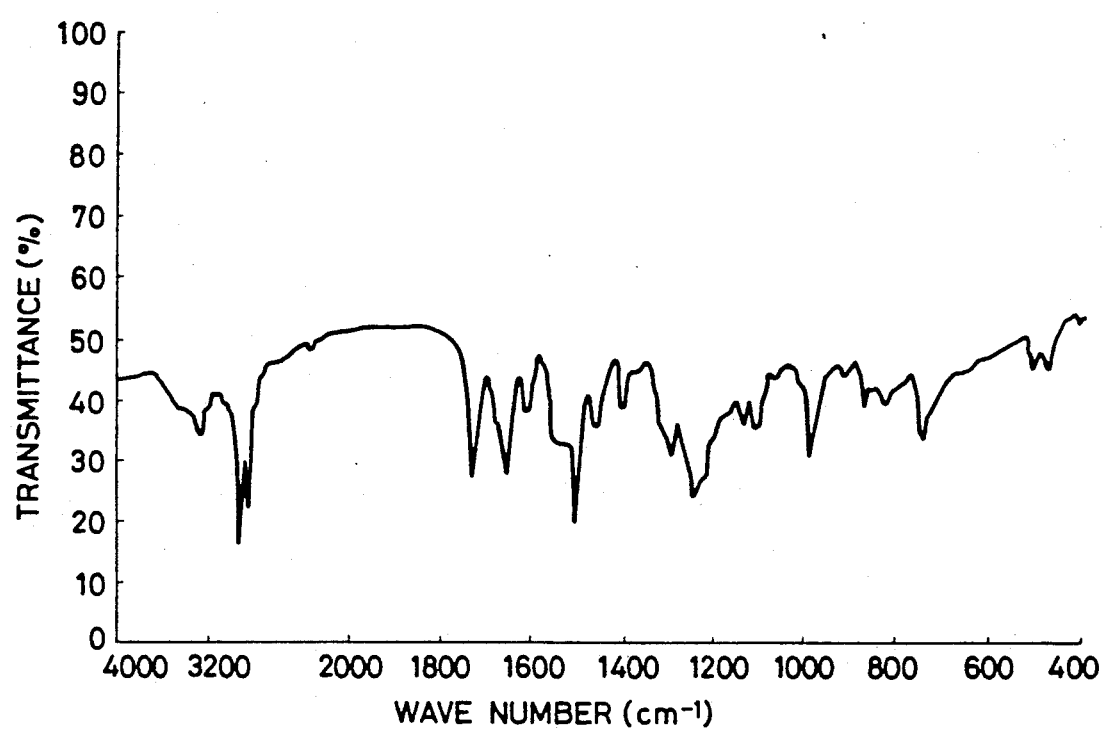
FIG. 20 shows an IR spectrum of the precursor obtained in Example 6.

As the IR chart obtained by KBr disc method is shown in FIG. 20, there appeared the absorption peaks characteristic of esters, amides I, II, and III, alkyl chains, and ethers.

Thermal Analysis (TGA-DTA)

Figure 21:
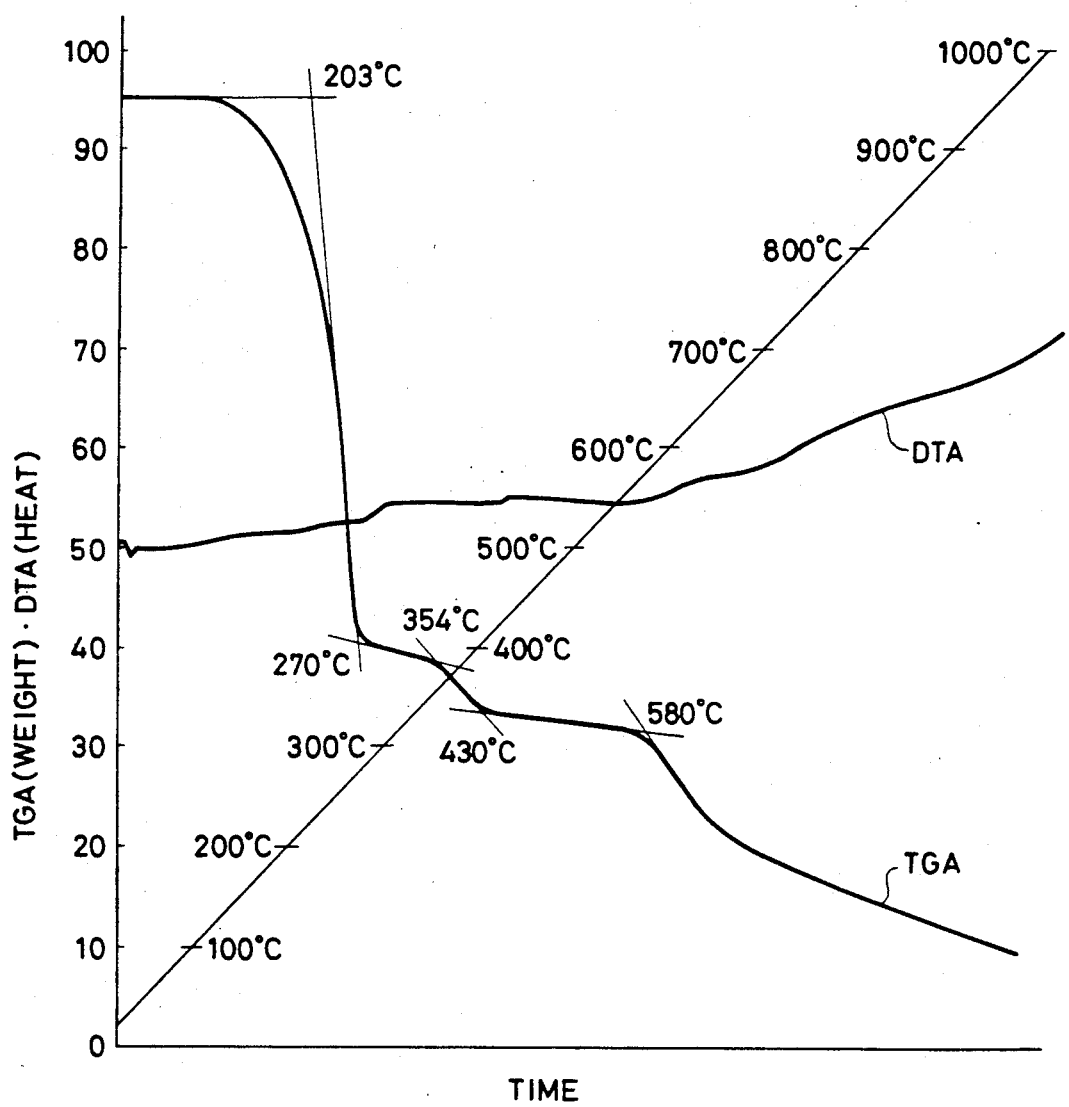
FIG. 21 shows the results of thermal analysis for the precursor obtained in Example 6.

The result obtained by measuring by the use of an RTG-DTA of type (H), manufactured by Rigaku Denki Co., Ltd., under the following conditions: TGA full scale, 10 mg; DTA full scale, 100 μV; maximum temperature, 1,000° C.; rate of heating, 10° C./min; and nitrogen stream of 30 ml/min is as shown in FIG. 21. In the TGA are observed inflection points at 203°, 270°, 354°, 403°, and 580° C., while in the DTA is observed no characteristic peak.

Measurement of Molecular Weight by GPC

A number average molecular weight of ca. 15,000 (reduced to polystyrene) was obtained by GPC measured in a mixed solvent of chloroform and N,N-dimethylacetamide (8:2).

EXAMPLE 7

In an 8:2 mixture (by volume) of distilled chloroform and distilled dimethylacetamide was dissolved 55.1 mg of the product obtained in Example 6 to prepare 25 ml of LB film spreading solution.

Figure 22:
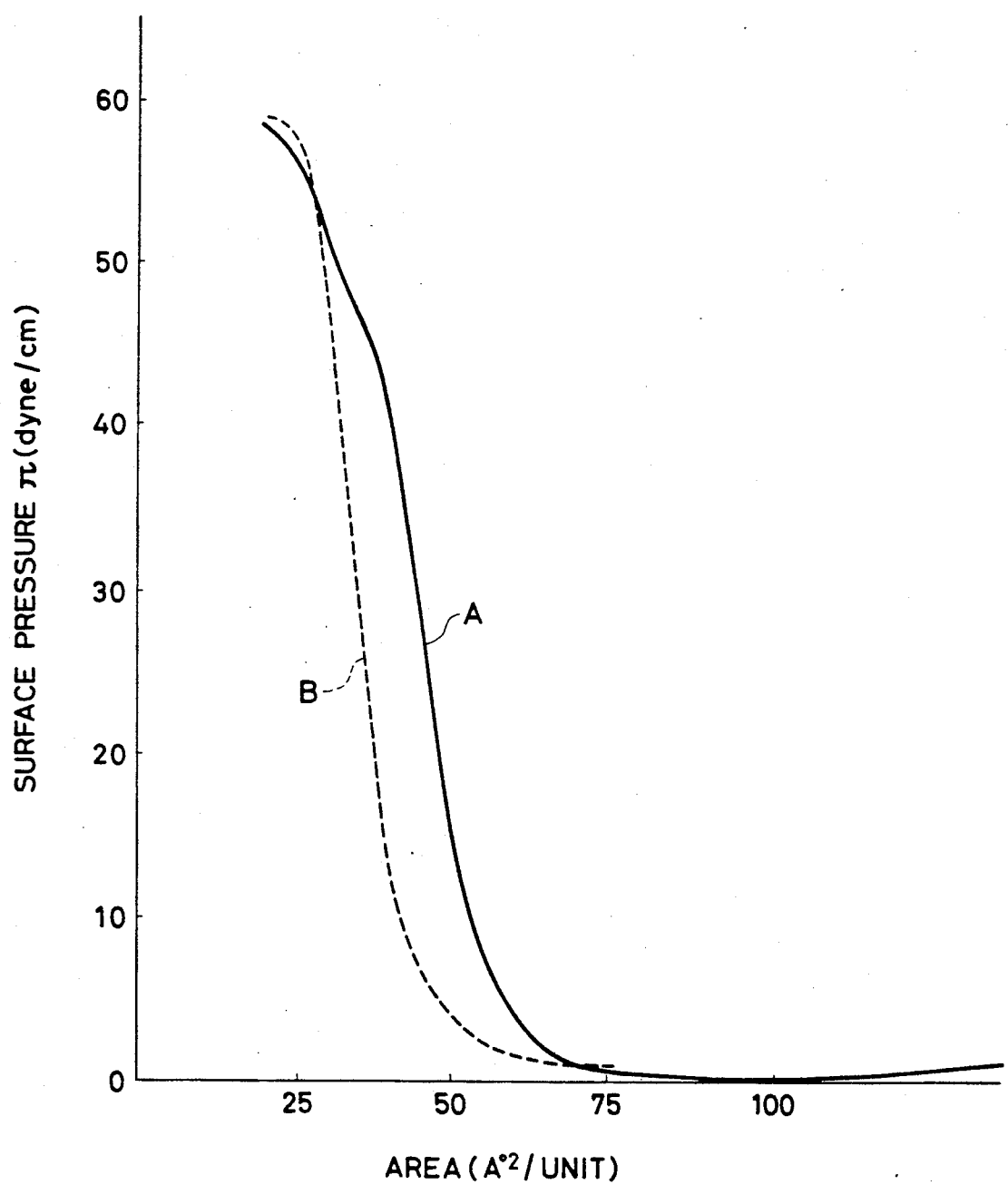
FIG. 22 is a graph showing the relationship between surface pressure and an area per recurring unit each of the precursor obtained in Example 6 and a 1:1 (by mole) mixture thereof with stearyl alcohol.

The relationship between surface pressure and area per recurring unit was measured at 20° C. on the surface of redistilled water, and the result shown in FIG. 22 was obtained. The surface pressure rose steeply at around 65 Å/unit, forming a good condensed film. The limiting area was 55 Å/unit, and the collapse pressure was 45 dyne/cm (FIG. 22-A). When the above described solution and a solution of stearyl alcohol having the same molar concentration as the above described solution were mixed in equal volumes and the surface pressure-area curve was evaluated by making the sum of the number of recurring units in the product obtained in Example 6 and the number of molecules of the stearyl alcohol equal to FIG. 22-A, the result as shown by B in FIG. 22 was obtained. It would be apparent that by the addition of stearyl alcohol the rise of the curve becomes still further steeper, and the collapse pressure also rises to ca. 60 dyne/cm, thus the film being stabilized.

The deposition on the glass substrate on which aluminum was vacuum evaporated or which was treated with silane coupling agent A-1100 or A-187 was found to be of Y-type whether stearyl alcohol was added or not and the deposited film obtained was equally good.

Further, when a 1:1 mixture (molar ratio) of the product obtained in Example 6 and stearyl alcohol was layered on a germanium substrate, and heated at 400° C. for one hour in a stream of nitrogen, there were observed the disappearance of the stearyl group and the appearance of five-numbered ring imide of 1790, 1710 $cm^{-1}$ according to FT-IR process.

EXAMPLE 8

The procedure of Example 6 was repeated to prepare a polyimide precursor, except for using stearic acid, ω-heptadecenoic acid, or octadecane in place of stearyl alcohol. When the surface pressure-area curve was evaluated in the same manner as in Example 7, it was found that the rise of the curve becomes steeper and the collapse pressure also increases by the addition of any of the above compounds similarly to the case of stearyl alcohol.

It was also found that the collapse pressure in the case of stearic acid or ω-heptadecenoic acid is substantially equal to that of the case of stearyl alcohol and superior to that of the case of octadecane.

When the film containing stearic acid, ω-heptadecenoic acid, or octadecane was built up on a glass substrate on which aluminum had been vacuum evaporated, a satisfactory built-up film of Y-type could be obtained.

EXAMPLE 9

A built-up film composed of 11, 21, 31, 41, or 51 layers was produced in the same manner as in Example 2 except for using a 1:1 (molar ratio) mixture of the compound of Example 6 and stearyl alcohol. A glass plate treated with a silane coupling agent, A-1100 (1%), on which an aluminum electrode was vacuum evaporated to a width of 0.5 mm, was used as a substrate.

After drying overnight, the film was heated at 400° C. in a nitrogen stream for 1 hour. An aluminum electrode having a width of 0.1 mm was formed on the film by vacuum evaporation in the direction perpendicular to the aluminum electrode formed on the substrate to prepare an MIM device as shown in FIG. 8.

Figure 23:
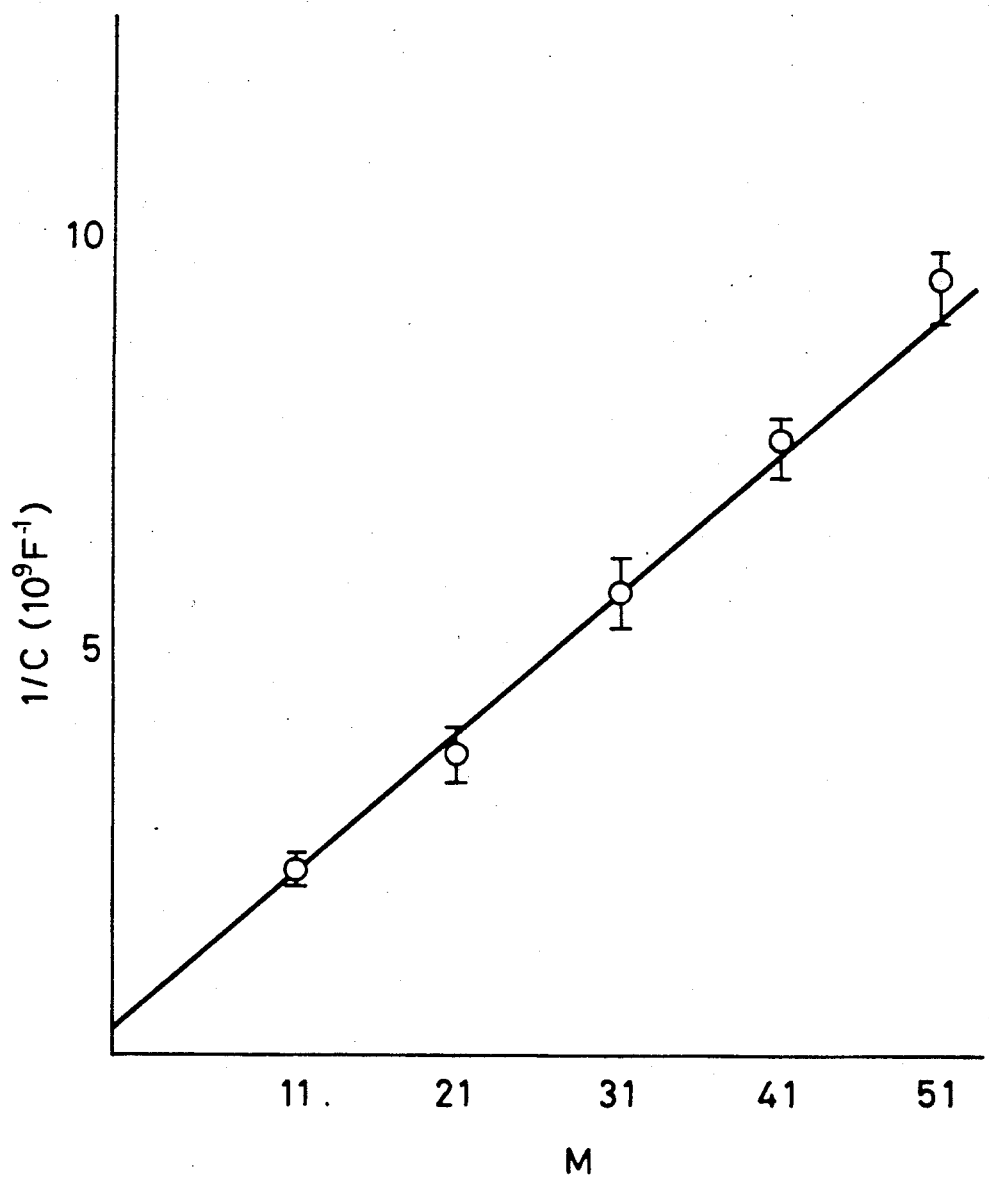
FIG. 23 is a graph obtained by plotting the reciprocal of capacitance of polyimide thin film obtained by imidizing a deposited precursor as ordinate and the number of precursor films deposited as abscissa.

The capacitance of the device was measured at a frequency of 1 kHz at room temperature and its reciprocal was plotted against the number of layers built up. The results are shown in FIG. 23. In FIG. 23, the bars indicate scatter of 10 data. The dissipation factor was about 0.02 in each case.

A built-up film composed of 11, 21, 31, 41, 51, 101, or 151 layers was prepared in the same manner as above and heated at 400° C. in a nitrogen stream for 1 hour. The resulting polyimide thin film had a thickness of about 50, 100, 150, 200, 250, 500, or 700 Å, respectively. An aluminum/polyimide thin film/aluminum device having a device area of 0.18 cm$^2$ was constructed using each of the built-up films. When an electric field of $1\times10^6$, $2\times10^6$, $3\times10^6$, $4\times10^6$, or $5\times10^6$ V/cm was applied to ten samples each of these films, none of the samples underwent breakdown. These results demonstrate that these films have a dielectric breakdown strength not less than $1\times10^6$ V/cm. Further, no change in breakdown strength was observed upon heating at 150° C. for 30 minutes.

Figure 24:
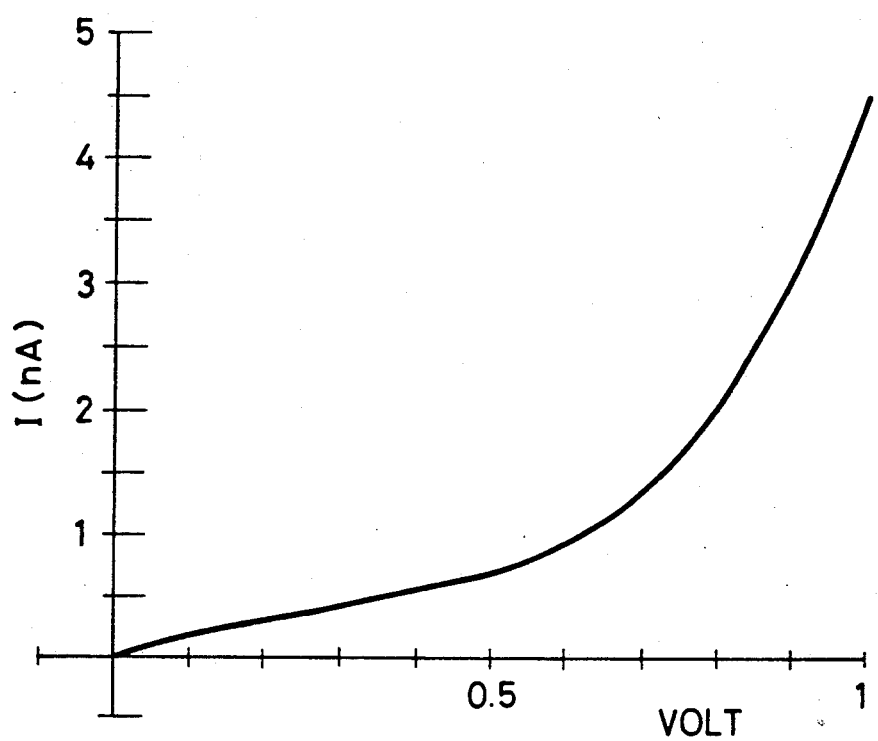
FIGS. 24 and 25 are graphs each showing the I (current) vs. V (voltage) characteristic of a polyimide thin film.
Figure 25:
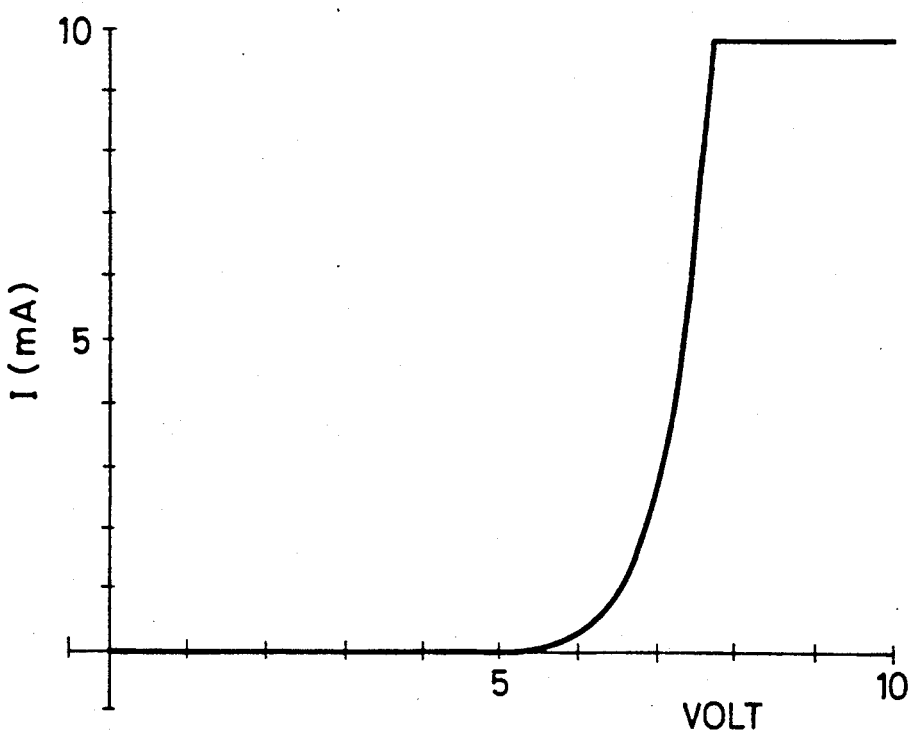

The I (current) $-$V (voltage) characteristic of the device including the polyimide thin film of about 100 Å in thickness is shown in FIGS. 24 and 25. As shown in the figures, the device shows conduction properties that follow Ohm's law up to the voltage of $0.5\times10^6$ V/cm and thereafter follow $\ln I \propto V^{\frac{1}{2}}$. FIG. 25 also proves that this film of about 100 Å withstands an electric field of 10 V, i.e., $1\times10^7$ V/cm. Therefore, the polyimide thin films in accordance with the present invention are suitable as insulating films in various electric-electronic devices.

EXAMPLE 10

An MIS type direct current-driven EL device having a structure of FIG. 3 was produced.

On a patterned ITO glass plate having a sheet resistance of 15 Ω/□ and a visible light transmittance of about 80% was formed a ZnS(Mn) layer by electron beam vacuum evaporation using ZnS containing 0.7% by weight Mn as a target. The pressure for vacuum evaporation was about $1\times10^{-6}$ Torr; the substrate temperature was about 170° C.; and the rate of film formation was about 10 Å/sec. The resulting ZnS(Mn) thin layer was a polycrystalline film preferentially oriented to the direction of the face (111) and had a thickness of about 0.1 μm. The resulting ZnS(Mn) layer was heat-treated at 600° C. for 1 hour under a nitrogen stream.

A 1:1 (by mole) mixture of the compound of Example 6 and stearyl alcohol was deposited on the thus treated glass substrate under the same conditions as in Example 9 to build up 21 layers. The resulting build-up was of nearly ideal Y-type. After drying for one day, the sample was heated at 400° C. for 1 hour in a nitrogen stream to effect imidation reaction. An aluminum layer was then formed thereon by vacuum evaporation in the direction perpendicular to the ITO electrode to thereby obtain an EL device having an MIS structure.

Figure 26:
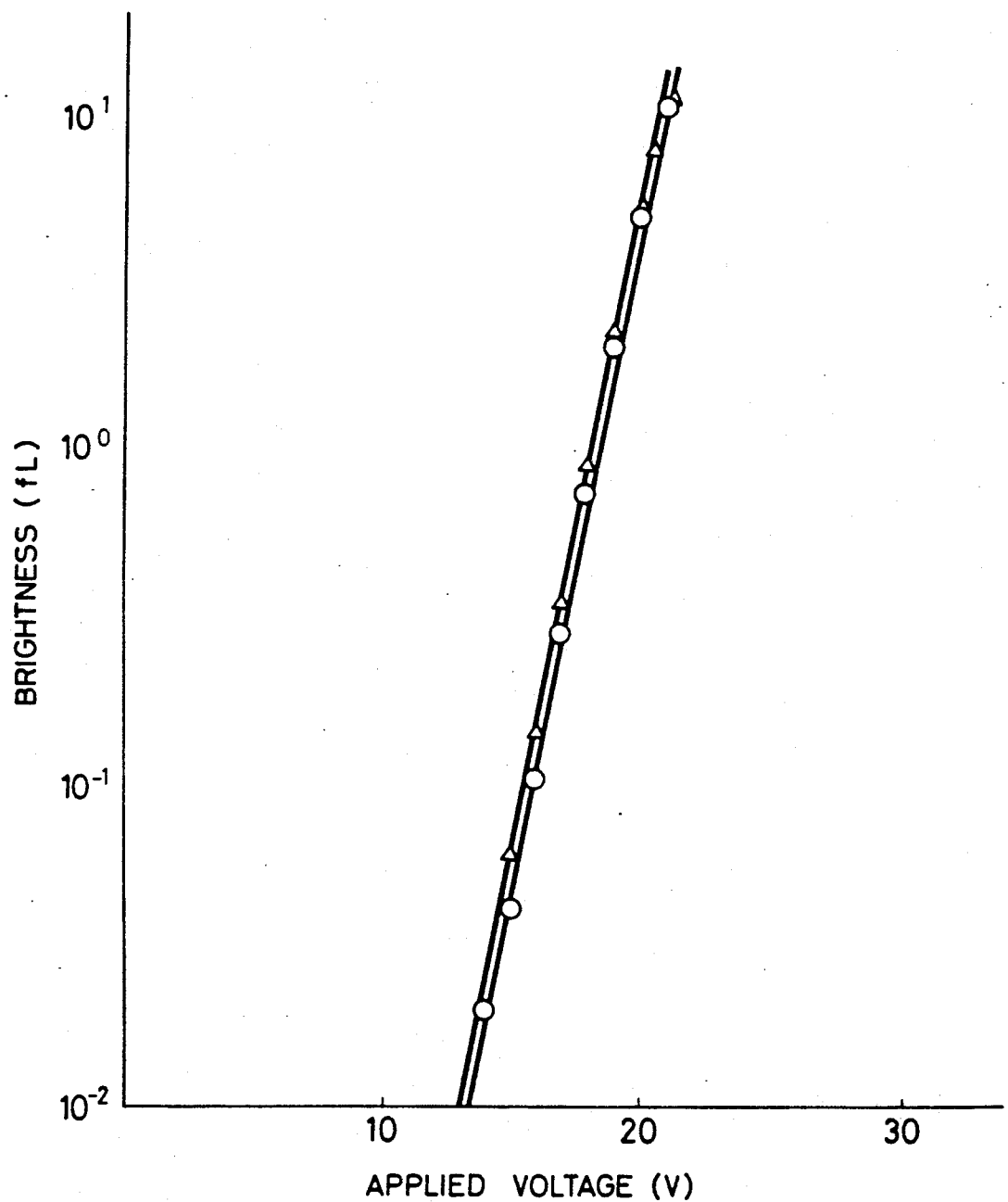
FIG. 26 shows the relationship between brightness and voltage of a direct current-driven EL device having a metal/insulating film/semiconductor (MIS) structure.

FIG. 26 shows the plots of brightness vs. voltage for two of the devices when a direct voltage was applied to the ITO electrode positively and to the aluminum electrode negatively. As can be seen from FIG. 26, the threshold voltage was 13 V, and the maximum brightness was 11 fL at 21 V with emission of a yellowish orange light. When the device was heated at 150° C. for 30 minutes, no change in initial performances was observed.

When an MS device of the similar structure but including no polyimide thin film was produced and a voltage was applied thereto, it underwent dielectric breakdown at a voltage of around 9 V and no emission was obtained.

Although not yet proved, it is considered that a high brightness at a low voltage as above obtained is attributable to (1) injection of hot electrons into ZnS(Mn) due to an electric field of the insulating film, (2) an improved dielectric breakdown strength of the device due to the presence of the insulating film having high dielectric breakdown strength, (3) reduction in interfacial states between ZnS:Mn and aluminum, and the like.

Thus, the example demonstrates that the polyimide thin film of the present invention effectively functions as an insulating film for devices having an MIS structure.

As described, since the electric-electronic devices according to the present invention contain the polyimide thin film having a thickness not more than 1000 Å and showing satisfactory insulating characteristics, the operating voltage can be reduced, and in particular, compound semiconductors that find difficult in forming in good insulating films can be utilized in the devices effectively.

Further, use of the polyimide thin film of the invention makes it possible to construct devices taking advantage of specific effects produced in the insulating film in a high electric field, such as hot electrons and a tunnel effect. Therefore, the present invention is extremely significant and beneficial in the industry.

While the invention has been described in detail and with reference to specific embodiments thereof, it will be apparent to one skilled in the art that various changes and modifications can be made therein without departing from the spirit and scope thereof.

What is claimed is:

1. An electric-electronic device comprising a heat-resistant polyimide thin film formed by a Langmuir-Blodgett method and having a thickness of not more than 1000 Å, and a dielectric breakdown strength of not less than $1\times10^6$ V/cm.

2. An electric-electronic device as in claim 1, wherein said polyimide thin film is obtained by building up an amphiphilic polyimide precursor on a substrate by a Langmuir-Blodgett process and imidizing the built-up film.

3. An electric-electronic device as in claim 1, wherein said device has a metal/insulating film/metal structure, said insulating film being the polyimide thin film.

4. An electric-electronic device as in claim 1, wherein said device has a metal/insulating film/semiconductor structure, said insulating film being the polyimide thin film.

5. An electric-electronic device comprising a polyimide thin film obtained by building up a film of an amphiphilic polyimide precursor on a substrate by a Langmuir-Blodgett process and imidizing the built-up film, wherein said amphiphilic polyimide precursor is represented by formula (I)

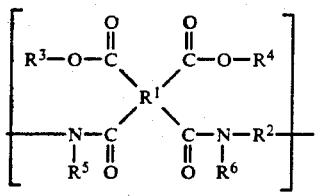

wherein $R^1$ is a tetravalent group having at least 2 carbon atoms, $R^2$ is a bivalent group having at least 2 carbon atoms, and each of $R^3$, $R^4$, $R^5$ and $R^6$ is independently selected from the group consisting of:
(1) hydrogen atom; and
(2) a monovalent group having 1 to 30 carbon atoms selected from the group consisting of an aliphatic group, an alicyclic group, an aromatic group, a group in which an aliphatic group is combined with an aromatic group, a group in which an aliphatic group is combined with an alicyclic group, said monovalent group being unsubstituted or substituted by a halogen atom, nitro group, amino group, cyano group, methoxy group or acetoxy group, provided that at least one of $R^3$, $R^4$, $R^5$ and $R^6$ has at least 12 carbon atoms, wherein said polyimide thin film has a thickness of not more than 1000 Å and a dielectric breakdown strength of not less than $1 \times 10^6$ V/cm.

6. An electric-electronic device as in claim 5, wherein said device has a metal/insulating film/metal structure, said insulating film being the polyimide thin film.

7. An electric-electronic device as in claim 5, wherein said device has a metal/insulating film/semiconductor structure, said insulating film being the polyimide thin film.